(12) United States Patent
Roth et al.

(10) Patent No.: US 7,604,995 B2
(45) Date of Patent: Oct. 20, 2009

(54) COMPOSITIONS, KITS, AND METHODS FOR STIMULATION OF HOMOLOGOUS RECOMBINATION

(75) Inventors: David B. Roth, New York, NY (US); Gregory S. Lee, New York, NY (US)

(73) Assignee: New York University, New York, NY (US)

( * ) Notice: Subject to any disclaimer, the term of this patent is extended or adjusted under 35 U.S.C. 154(b) by 4 days.

(21) Appl. No.: 10/887,593

(22) Filed: Jul. 9, 2004

(65) Prior Publication Data
US 2005/0069921 A1    Mar. 31, 2005

Related U.S. Application Data

(60) Provisional application No. 60/486,352, filed on Jul. 11, 2003, provisional application No. 60/487,211, filed on Jul. 14, 2003, provisional application No. 60/558,326, filed on Mar. 31, 2004.

(51) Int. Cl.
C12N 15/87 (2006.01)
C12N 15/00 (2006.01)
C12N 15/64 (2006.01)
C12P 19/34 (2006.01)

(52) U.S. Cl. ................... 435/463; 435/455; 435/91.4; 435/91.1

(58) Field of Classification Search .................. None
See application file for complete search history.

(56) References Cited

U.S. PATENT DOCUMENTS 5,756,323 A * 5/1998 Kallenbach et al. ............ 435/6

OTHER PUBLICATIONS

Neiditch, M. et al., "The V(D)J Recombinase Efficiently Cleaves and Transposes Signal Joints", Mol. Cell, Apr. 2002, vol. 9: pp. 871-878.*
Babinet, C. et al., "Genome engineering via homologous recombination in mouse embryonic stem cells: ana amzingly versatile tool for the study of mammalian biology", 2001, An. Acad. Bras. Cienc., vol. 73: pp. 365-383.*
Shibata, T. et al., "Homologous genetic recombination as an intrinsic dynamic property of a DNA structure induced by RecA/Rad51-family proteins: A possible advantage of DNA over RNA as genomic material", 2001, PNAS, vol. 98: pp. 8425-8432.*
Weterings, E. et al., "The endless tale of non-homologous end-joining", 2008, Cell Res., vol. 18: pp. 114-124.*
Roth, D., "Restraining the V(D)J Recombinase", 2003, Nat. Rev. Immunol., vol. 3: pp. 656-666.*
Declaration of Dr. David Roth, May 21, 2009, 2 pages.*
Gonda, D. et al., "By Searching Processively RecA Protein Pairs DNA Molecules That Share a Limited Stretch of Homology", 1983, Cell., vol. 34: pp. 647-654.*
Agrawal, A., and Schatz, D. G. (1997). RAG1 and RAG2 form a stable postcleavage synaptic complex with DNA containing signal ends in V(D)J recombination. Cell 89, 43-53.
Agrawal, A., Eastman, Q. M., and Schatz, D. G. (1998). Transposition mediated by RAG1 and RAG2 and its implications for the evolution of the immune system. Nature 394, 744-751.
Arcangioli, B. (1998). A site- and strand-specific DNA break confers asymmetric switching potential in fission yeast. Embo J 17, 4503-4510.
Arcangioli, B., and de Lahondes, R. (2000). Fission yeast switched mating type by a replication-recombination coupled process. Embo J 19, 1389-1396.
Baumann, P., and West, S. C. (1998). DNA End-joining catalyzed by human cell-free extracts. Proc Natl Acad Sci USA 95, 14066-14070.
Brandt, V. L., and Roth, D. B. (2002). A recombinase diversified: new functions of the RAG proteins. Curr Opin Immunol 14, 224-229.
Chen, H. T., Bhandoola, A., Difilippantonio, M. J., Zhu, J., Brown, M. J., Tai, X., Rogakou, E. P., Brotz, T. M., Bonner, W. M., Ried, T., and Nussenzweig, A. (2000). Response to RAG-mediated VDJ cleavage by NBS1 and gamma-H2AX. Science 290, 1962-1965.
Cuomo, C. A., Mundy, C. L., and Oettinger, M. A. (1996). DNA sequence and structure requirements for cleavage of V(D)J recombination signal sequences. Molecular and Cellular Biology 16, 5683-5690.
Ferguson, D. O., and Alt, F. W. (2001). DNA double strand break repair and chromosomal translocation: lessons from animal models. Oncogene 20, 5572-5579.
Ferguson, D. O., Sekiguchi, J. M., Chang, S., Frank, K. M., Gao, Y., DePinho, R. A., and Alt, F. W. (2000). The nonhomologous end-joining pathway of DNA repair is required for genomic stability and the suppression of translocations. Proc Natl Acad Sci U S A 97, 6630-6633.
Frank-Vaillant, M., and Marcand, S. (2002). Transient stability of DNA ends allows nonhomologous end joining to precede homologous recombination. Mol Cell 10, 1189-1199.
Goedecke, W., Eijpe, M., Offenberg, H. H., van Aalderen, M., and Heyting, C. (1999). Mre11 and Ku70 interact in somatic cells, but are differentially expressed in early meiosis. Nat Genet 23, 194-198.

(Continued)

Primary Examiner—Michael Burkhart
(74) Attorney, Agent, or Firm—Kenneth I. Kohn

(57) ABSTRACT

A method of stimulating homologous recombination by creating at least one nick in a targeted polynucleotide sequence. Wherein nonhomologous recombination is suppressed resulting in increasing the ratio of targeted to nontargeted events. A method of increasing double strand break-initiated gene targeting by inducing a nick in a targeted polynucleotide sequence, wherein overall recombination levels are increased. A method of increasing homologous recombination employing a recombinase that releases the ends in living cells by stimulating homolgous recombination to higher levels than those attainable with standard nucleases. A composition for stimulating homologous recombination including a nicking mechanism for creating nicks in a polynucleotide, wherein the nicking mechanism stimulates homologous recombination. A composition for stimulating homologous recombination including a nicking endonucleases. Various kits for stimulating homologous recombination. A method for modulating and channeling site-specific DNA stand breaks by shepherding the DNA strand breaks to particular recombination pathways.

6 Claims, 14 Drawing Sheets

OTHER PUBLICATIONS

Grawunder, U., and Lieber, M, R. (1997). A complex of RAG-1 and RAG-2 proteins persists on DNA after single-strand cleavage at V(D)J recombination signal sequences. Nucleic Acids Res 25, 1375-1382.

Haber, J. E. (1999). DNA repair. Gatekeepers of recombination. Nature 398, 665, 667.

Han, J.-O., Erskine, L. A., Purugganan, M. M., Stamato, T. D., and Roth, D. B. (1998). V(D)J recombination intermediates and non-standard products in XRCC4-deficient cells. Nucleic Acids Res 26, 3769-3775.

Han, J.-O., Steen, S. B., and Roth, D. B. (1997). Ku86 is not required for protection of signal ends or for formation of nonstandard V(D)J recombination products. Mol Cell Biol 17, 2226-2234.

Hesse, J. E., Lieber, M. R., Gellert, M., and Mizuuchi, K. (1987). Extrachromosomal DNA substrates in pre-B cells undergo inversion or deletion at immunoglobulin V(D)J joining signals. Cell 49, 775-783.

Hiom, K., and Gellert, M. (1998). Assembly of a 12/23 paired signal complex: A critical control point in V(D)J recombination. Molecular Cell 1, 1011-1019.

Hiom, K., Melek, M., and Gellert, M. (1998). DNA transposition by the RAG1 and RAG2 proteins: a possible source of oncogenic translocations. Cell 94, 463-470.

Huye, L. E., Purugganan, M. M., Jiang, M. M., and Roth, D. B. (2002). Mutational analysis of all conserved basic amino acids in RAG-1 reveals catalytic, step arrest, and joining-deficient mutants in the V(D)J recombinase. Mol Cell Biol 22, 3460-3473.

Jasin, M. (1996). Genetic manipulation of genomes with rare-cutting endonucleases. Trends Genet 12, 224-228.

Jones, J. M., and Gellert, M. (2001). Intermediates in V(D)J recombination: a stable RAG1/2 complex sequesters cleaved RSS ends. Proc Natl Acad Sci U S A 98, 12926-12931.

Kabotyanski, E. B., Gomelsky, L., Han, J.-O., Stamato, T. D., and Roth, D. B. (1998). Double-strand break repair in Ku86- and XRCC4-deficient cells. Nucleic Acids Res 26, 5333-5342.

Landree, M. A., Wibbenmeyer, J. A., and Roth, D. B. (1999). Mutational analysis of RAG-1 and RAG-2 identifies three active site amino acids in RAG-1 critical for both cleavage steps of V(D)J recombination. Genes Dev 13, 3059-3069.

Lee, G. S., M.B. Neiditch, S.S. Salus, and D.B. Roth, *RAG proteins shepherd double-strand breaks to a specific pathway, suppressing error-prone repair, but RAG nicking initiates homologous recombination*. Cell, 2004. 117, 171-84.

Lee, S. S., Fitch, D., Flajnik, M. F., and Hsu, E. (2000). Rearrangement of immunoglobulin genes in shark germ cells. J Exp Med 191, 1637-1648.

Leu, T. M., Eastman, Q. M., and Schatz, D. G. (1997). Coding joint formation in a cell-free V(D)J recombination system. Immunity 7, 303-314.

Lewis, S. M. (1994). The mechanism of V(D)J joining: Lessons from molecular, immunological and comparative analyses. AdvImmunol 56, 27-150.

Lewis, S. M., and Wu, G. E. (2000). The old and the restless. J Exp Med 191, 1631-1636.

Moynahan, M. E., Pierce, A. J., and Jasin, M. (2001). BRCA2 is required for homology-directed repair of chromosomal breaks. Mol Cell 7, 263-272.

Pâques, F., and Haber, J. E. (1999). Multiple pathways of recombination induced by double-strand breaks in *Saccharomyces cerevisiae*. Microbiol Mol Biol Rev 63, 349-404.

Perkins, E. J., Nair, A., Cowley, D. O., Van Dyke, T., Chang, Y., and Ramsden, D. A. (2002). Sensing of intermediates in V(D)J recombination by ATM. Genes Dev 16, 159-164.

Pierce, A. J., Hu, P., Han, M., Ellis, N., and Jasin, M. (2001). Ku DNA end-binding protein modulates homologous repair of double-strand breaks in mammalian cells. Genes Dev 15, 3237-3242.

Pierce, A. J., Johnson, R. D., Thompson, L. H., and Jasin, M. (1999). XRCC3 promotes homology-directed repair of DNA damage in mammalian cells. Genes Dev 13, 2633-2638.

Qiu, J. X., Kale, S. B., Yarnell Schultz, H., and Roth, D. B. (2001). Separation-of-function mutants reveal critical roles for RAG2 in both the cleavage and joining steps of V(D)J recombination. Mol Cell 7, 77-87.

Raghavan, S. C., Kirsch, I. R., and Lieber, M. R. (2001). Analysis of the V(D)J recombination efficiency at lymphoid chromosomal translocation breakpoints. J Biol Chem 276, 29126-29133.

Ramsden, D. A., McBlane, J. F., van Gent, D. C., and Gellert, M. (1996). Distinct DNA sequence and structure requirements for the two steps of V(D)J recombination signal cleavage. EMBO J 15, 3197-3206.

Ramsden, D. A., Paull, T. T., and Gellert, M. (1997). Cell-free V(D)J recombination. Nature 388, 488-491.

Richardson, C., and Jasin, M. (2000). Coupled homologous and nonhomologous repair of a double-strand break preserves genomic integrity in mammalian cells. Mol Cell Biol 20, 9068-9075.

Ristic, D., Modesti, M., Kanaar, R., and Wyman, C. (2003). Rad52 and Ku bind to different DNA structures produced early in double-strand break repair. Nucleic Acids Res 31, 5229-5237.

Roth, D. B. (2000). From lymphocytes to sharks: V(D)J recombinase moves to the germline. Genome Biol 1, 1014.1011-1014.

Roth, D. B. (2002). Amplifying mechanisms of lymphomagenesis. Mol Cell 10, 1-2.

Roth, D. B., and Wilson, J. H. (1985). Relative rates of homologous and nonhomologous recombination in transfected DNA. Proc Natl Acad Sci U S A 82, 3355-3359.

Roth, D. B., and Wilson, J. H. (1986). Nonhomologous recombination in mammalian cells: role for short sequence homologies in the joining reaction. Mol Cell Biol 6, 4295-4304.

Sadofsky, M. J., Hesse, J. E., and Gellert, M. (1994a). Definition of a core region of RAG-2 that is functional in V(D)J recombination. Nucleic Acids Res 22, 1805-1809.

Sadofsky, M. J., Hesse, J. E., McBlane, J. F., and Gellert, M. (1994b). Expression and V(D)J recombination activity of mutated RAG-1 proteins. Nucleic Acids Res 22, 550.

Spanopoulou, E., Zaitseva, F., Wang, F.-H., Santagata, S., Baltimore, D., and Panayotou, G. (1996). The homeodomain region of Rag-1 reveals the parallel mechanisms of bacterial and V(D)J recombination. Cell 87, 263-276.

Steen, S. B., Gomelsky, L., and Roth, D. B. (1996). The 12/23 rule is enforced at the cleavage step of V(D)J recombination in vivo. Genes to Cells 1, 543-553.

Steen, S. B., Gomelsky, L., Speidel, S. L., and Roth, D. B. (1997). Initiation of V(D)J recombination in vivo: role of recombination signal sequences in formation of single and paired double-strand breaks. EMBO Journal 16, 2656-2664.

Steen, S. B., Han, J.-O., Mundy, C., Oettinger, M. A., and Roth, D. B. (1999). Roles of the "dispensable" portions of RAG-1 and RAG-2 in V(D)J recombination. Molecular and Cellular Biology 19, 3010-3017.

Strathem, J. N., Weinstock, K. G., Higgins, D. R., and McGill, C. B. (1991). A novel recombinator in yeast based on gene II protein from bacteriophage f1. Genetics 127, 61-73.

Takata, M., Sasaki, M. S., Sonoda, E., Morrison, C., Hashimoto, M., Utsumi, H., Yamaguchi-Iwai, Y., Shinohara, A., and Takeda, S. (1998). Homologous recombination and non-homologous end-joining pathways of DNA double-strand break repair have overlapping roles in the maintenance of chromosomal integrity in vertebrate cells. EMBO 17, 5497-5508.

Tsai, C. L., Drejer, A. H., and Schatz, D. G. (2002). Evidence of a critical architectural function for the RAG proteins in end processing, protection, and joining in V(D)J recombination. Genes Dev 16, 1934-1949.

Van Dyck, E., Stasiak, A. Z., Stasiak, A., and West, S. C. (1999). Binding of double-strand breaks in DNA by human Rad52 protein. Nature 398, 728-731.

Verkaik, N. S., Esveldt-van Lange, R. E., van Heemst, D., Bruggenwirth, H. T., Hoeijmakers, J. H., Zdzienicka, M. Z., and van Gent, D. C. (2002). Different types of V(D)J recombination and end-joining defects in DNA double-strand break repair mutant mammalian cells. Eur J Immunol 32, 701-709.

Villa, A., Sobacchi, C., Notarangelo, L. D., Bozzi, F., Abinun, M., Abrahamsen, T. G., Arkwright, P. D., Baniyash, M., Brooks, E. G., Conley, M. E., et al. (2001). V(D)J recombination defects in lymphocytes due to RAG mutations: severe immunodeficiency with a spectrum of clinical presentations. Blood 97, 81-88.

Wake, C. T., Gudewicz, T., Porter, T., White, A., and Wilson, J. H. (1984). How damaged is the biologically active subpopulation of transfected DNA? Mol Cell Biol 4, 387-398.

Yarnall Schultz, H., Landree, M. A., Qiu, J. X., Kale, S. B., and Roth, D. B. (2001). Joining-deficient RAG1 mutants block V(D)J recombination in vivo and hairpin opening in vitro. Mol Cell 7, 65-75.

Zhu, C., Bogue, M. A., Lim, D.-S., Hasty, P., and Roth D. B. (1996). Ku86-deficient mice exhibit severe combined immunodeficiency and defective processing of V(D)Jrecombination intermediates. Cell 86, 379-389.

Zhu, C., Mills, K. D., Ferguson, D. O., Lee, C., Manis, J., Fleming, J., Gao, Y., Morton, C. C., and Alt, F. W. (2002). Unrepaired DNA breaks in p53-deficient cells lead to oncogenic gene amplification subsequent to translocations. Cell 109, 811-821.

* cited by examiner

1) RAG binding, nicking

2) Synaptic complex formation

3) Hairpin formation, cleavage

Postcleavage complex (PCC)

4) Hairpin opening, joining

Coding Joint   Signal Joint

Joining-deficient RAG mutants tested in the CFP assay.

Supplemental Table 1. Joining-deficient RAG mutants tested in the CFP assay

| RAG-1 mutants | RAG-2 mutants |
|---|---|
| R401A/R402A | K34A |
| R440A | K56A/K58A |
| E423Q | R73A |
| E547Q | H94A/K97A |
| S723A | K118A/K119A |
| R838A/K839A/R840A | R167A |
| K980A | R229A |
|  | R235A/R237A |
|  | K312A/H313A/K315A |

Fig. 13

SEQUENCE LISTING

<160> NUMBER OF SEQ ID NOS: 3

<210> SEQ ID NO 1
<211> LENGTH: 28
<212> TYPE: DNA
<213> ORGANISM: Artificial
<220> FEATURE:
<223> OTHER INFORMATION: substrate

<400> SEQUENCE: 1
cacagtgcta cagactggaa caaaaacc                                   28

<210> SEQ ID NO 2
<211> LENGTH: 28
<212> TYPE: DNA
<213> ORGANISM: Artificial
<220> FEATURE:
<223> OTHER INFORMATION: Primer

<400> SEQUENCE: 2
cagttaataa cagaaaataa gccaggcc                                   28

<210> SEQ ID NO 3
<211> LENGTH: 32
<212> TYPE: DNA
<213> ORGANISM: Artificial
<220> FEATURE:
<223> OTHER INFORMATION: Primer

<400> SEQUENCE: 3
caaaatcaag ataatacccc ataattaaca gg                              32

COMPOSITIONS, KITS, AND METHODS FOR STIMULATION OF HOMOLOGOUS RECOMBINATION

CROSS REFERENCE TO RELATED APPLICATIONS

This application claims the benefit of priority under 35 U.S.C. Section 119(e) of U.S. Provisional Patent Application No. 60/486,352, filed Jul. 11, 2003, U.S. Provisional Patent Application No. 60/487,211, filed Jul. 14, 2003, and U.S. Provisional Patent Application No. 60/558,326, filed Mar. 31, 2004, all of which are incorporated herein by reference.

BACKGROUND OF THE INVENTION

1. Technical Field

The present invention relates to the field of molecular biology and more specifically towards gene targeting by homologous recombination.

2. Background Art

Gene targeting by homologous recombination is one of the most important tools of modern molecular biology. Gene targeting can generate targeted "knockout" or "knock-in" mutations in a variety of model organisms such as mice, which facilitates the development of mouse models of human genetic disorders. Gene targeting can also be utilized to correct inherited diseases in humans through gene therapy.

Generally, homologous recombination repairs double strand breaks made in meiotic prophase or during the S and G2 phases of the cell cycle, whereas non-homologous end joining repairs double strand breaks generated in the absence of a sister chromatid (Goedecke et al., 1999; Pâques and Haber, 1999; Takata et al., 1998). However, this division of labor is not absolute. Several lines of evidence indicate that these pathways can act contemporaneously or even in concert. For example, homologous recombination can occur during G1 (Fabre, 1978), non-homologous end joining and homologous recombination compete for repair of transfected linear DNA molecules (Roth and Wilson, 1985), disabling one pathway increases the activity of the other (Pierce et al., 2001), and the two mechanisms can act in a coupled fashion to repair a double strand breaks (Richardson and Jasin, 2000). The precise manner in which a particular repair pathway is selected to repair a given DSB, or even whether such a selection is made, has remained unknown. Yet, the choice of repair mechanism can serve as an important control point in various types of reactions involving double strand break intermediates. One model posits that the choice of pathway is essentially stochastic, determined by whether the broken ends are bound by Ku or by, for example, Rad52 (leading to NHEJ or homologous recombination, respectively) (Goedecke et al., 1999; Van Dyck et al., 1999; Haber, 1999). Alternatively, it has been proposed that if the ends remain intact they are available for NHEJ, but 5' strand resection can cause homologous recombination to occur (Frank-Vaillant and Marcand, 2002).

Recent scanning force microscopy studies indicate that Rad52 and Ku actually prefer different DNA substrates, and suggest that resection precedes Rad52 binding (Ristic et al., 2003). The identity of the "gatekeeper" molecule(s) that control this critical choice remains an open question. Adding to the puzzle is evidence suggesting that there can be other repair pathways, for example, the poorly characterized "alternative NHEJ" pathway that operates in the absence of classical NHEJ (i.e., Ku, XRCC4, DNA ligase IV, Artemis, and the DNA-dependent protein kinase catalytic subunit (DNA-PKcs)) (reviewed in Ferguson and Alt, 2001; Roth, 2003).

There are indeed mechanisms to guide broken DNA ends to an appropriate pathway, which have been discovered in the context of a recombination system that introduces site-specific double strand breaks and depends upon repair by a particular pathway to rejoin the DNA ends:V(D)J recombination. As the DNA rearrangement process that assembles antigen receptor genes during lymphocyte differentiation, V(D)J recombination relies on classical NHEJ to join site-specific double strand breaks. It was recently discovered that the V(D)J recombinase (the RAG proteins) shepherds the double-strand breaks to the classical NHEJ pathway [Lee et al., Cell, 2004).

As shown in FIG. 1, recombination is initiated by the RAG-1 and RAG-2 proteins, which introduce nicks at recombination signal sequences. Upon synapsis, the RAG proteins convert these nicks to double strand breaks, leaving four ends (two hairpinned coding ends and two blunt signal ends) (Roth, 2003). Whereas signal ends are blunt ends that can be directly joined, the covalently sealed hairpins must be opened and processed before the coding ends can be joined. End-processing and joining are carried out by the classical NHEJ factors (Roth, 2003) along with the help of the RAG proteins themselves, which maintain the ends in a post-cleavage complex in vitro (Agrawal and Schatz, 1997; Hiom and Gellert, 1998; Jones and Gellert, 2001) and in vivo (Qiu et al., 2001; Yarnall Schultz et al., 2001; Huye et al., 2002). In vivo studies of NHEJ mutants and mutant RAG proteins that have defects in joining demonstrate that the post-cleavage complex serves as a scaffold for the four ends to facilitate repair (Zhu et al., 1996; Qiu et al., 2001; Yarnall Schultz et al., 2001; Brandt and Roth, 2002; Huye et al., 2002).

Double strand breaks created during V(D)J recombination are deliberately shepherded by the RAG post-cleavage complex into a specific nonhomologous end joining pathway and the RAG post-cleavage complex prevents RAG-generated double-strand breaks from being repaired by alternative joining pathways. Mutations in RAG-1 disrupt the post-cleavage complex in a manner to allow double strand breaks to escape from the nonhomologous end-joining pathway and participate in homologous recombination.

As is well known in the art, current methods of gene targeting utilize a cell's endogenous homologous recombination machinery to integrate a gene. In prior studies, it was realized that linearizing the gene within the homology region greatly stimulates targeting by homologous recombination, and virtually all gene targeting protocols involve generating a double-strand break in the targeting vector (Vasquez, K M et al. *Proc Nat Acad Sci.* 98(15) 8403-8410). Double-strand breaks are common intermediates in a variety of genetic recombination processes. Double-strand breaks, however, are damaging toward chromosomal integrity because they cause aberrant chromosome rearrangements as well as deletion of essential genetic information. Therefore, targeted integrations are typically quite rare, occurring at a rate of approximately one event per $10^5$ to $10^7$ transfected cells (Sargent, R G and Wilson J H *Curr. Res. Mol. Ther.* 1: 584-692). Moreover, undesired and non-targeted events are always much more frequent than the desired homologous integration events. In somatic cells, nontargeted integrants are at least 1000-fold more frequent than targeted events (Sargent, R G and Wilson J H *Curr. Res. Mol. Ther.* 1 584-692). Although this ratio is more favorable in mouse embryonic stem cells, hundreds of integration events must still be searched to detect the desired targeted clone. As a result, a large amount of reagents, time, and energy must be expended to achieve the detection of the desired clone. Thus, even a modest (2-fold) increase in the ratio of targeted to non-targeted genetic modification events would be commercially useful.

The non-targeted integrations result from joining of the broken ends of the linearized targeting vector to endogenous chromosomal breaks by the non-homologous end-joining (NHEJ) pathway. In essence, these non-targeted integrations are necessary byproducts of linearizing the targeting vector to stimulate homologous recombination. In other words, placing a double-strand break in the targeted gene stimulates both the homologous recombination of the targeted gene and the undesired, non-targeted integrations. A modest increase in efficiency (around 5-fold) is gained through the use of positive and negative selection techniques; however, efficiency is still quite low. Thus, the identification of targeted clones is a significant hurdle in the standard practice of generating targeted ES cells, which are the precursors of "knockout" and "knock-in" mice, and is often prohibitively difficult for somatic cells.

Accordingly, there is a need for compositions, kits, and methods useful in stimulating homologous recombination and therefore useful in identifying targeted clones. More specifically, there is a need for improved gene targeting methods by homologous recombination wherein double-strand breaks are avoided. Further, there is a need for mutant or non-mutant proteins and compositions that stimulate homologous recombination.

SUMMARY OF THE INVENTION

The present invention provides methods, compositions, kits, and mechanisms for initiating or inducing homologous recombination. The present invention induces and/or modulates homologous recombination utilizing a nicking mechanism that create nicks in a polynucleotide sequence. Specifically, the present invention provides a method of stimulating homologous recombination by creating at least one nick in a targeted polynucleotide sequence. Additionally, the present invention provides a composition for stimulating homologous recombination including a nicking mechanism for creating nicks in a polynucleotide, wherein the nicking mechanism stimulates homologous recombination. The present invention also provides a kit and pharmaceutical composition for stimulating homologous recombination. The present invention provides methods relating to stimulation of homologous recombination. Further, the present invention provides kits including expression vectors. Finally, the present invention provides a method of gene targeting and a method for modulating and channeling site-specific DNA stand breaks by shepherding DNA strand breaks to particular recombination pathways.

BRIEF DESCRIPTION OF THE DRAWINGS

Other advantages of the present invention will be readily appreciated as the same becomes better understood by reference to the following detailed description when considered in connection with the accompanying drawings wherein:

FIG. 13 is a table illustrating joining-deficient RAG mutants tested in the CFP assay.

DETAILED DESCRIPTION OF THE INVENTION

Generally, the present invention is directed towards methods, mechanisms, compositions, and kits for initiating, modulating, and/or stimulating homologous recombination. Initiation, modulation, and/or stimulation of homologous recombination occur through double strand breaks (hereinafter, "DSB"), single strand breaks (hereinafter, "SB" or "nicks"), or combinations thereof. Moreover, the present invention improves achieving targeted integrations and decreasing the randomness of undesired, non-targeted integrations.

Previous studies have implicated site-specific nicks in stimulating homologous recombination in *S. cerevisiae* (using a coliphage nicking enzyme) (Strathern et al., 1991) and during mating type switching in fission yeast (Arcangioli, 1998). In neither instance could it be determined whether nicks themselves or subsequent DSB stimulate homologous recombination. In the case of *S. pombe* mating type switching it is suggested that the initiating lesions are DSB generated from the nicks by DNA replication (Arcangioli and de Lahondes, 2000).

Figure 7:
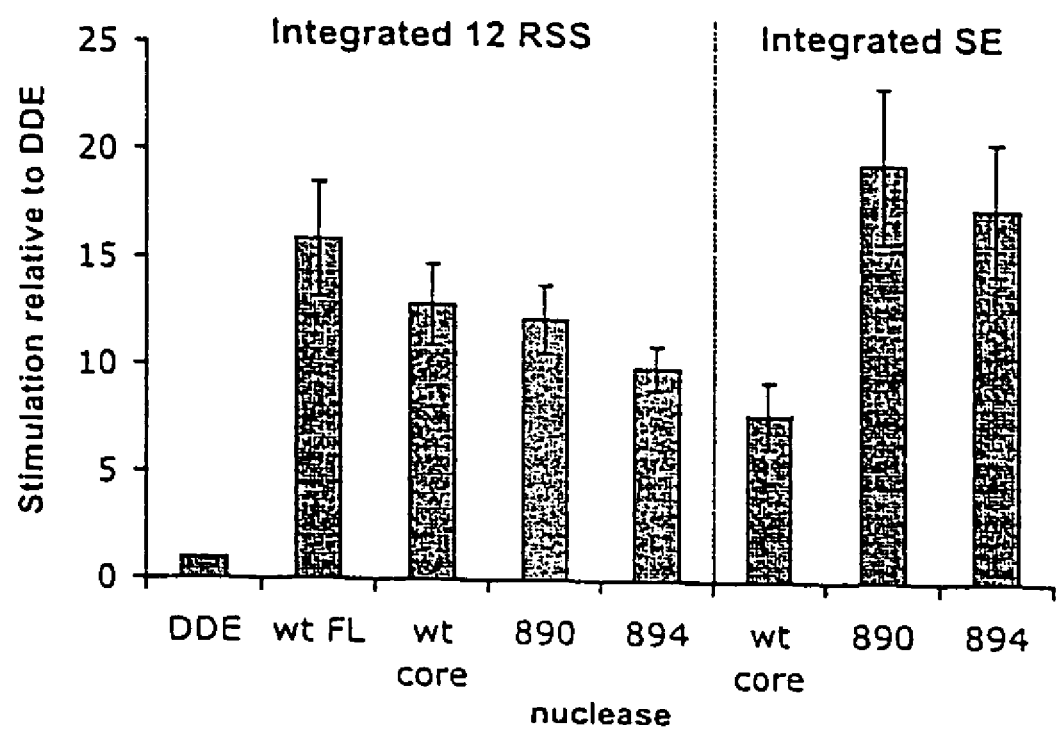
FIG. 7 illustrates that RAG-generated nicks stimulate homologous recombination on integrated substrates. The graph shows the relative stimulation of CFP expression by full-length and wild-type core RAG proteins, as well as nick-only mutant RAG proteins, in a cell line containing the single RSS substrate stably integrated in the chromosome. Nick-only mutants stimulating homologous recombination on an integrated SE substrate is shown.
Figure 8:
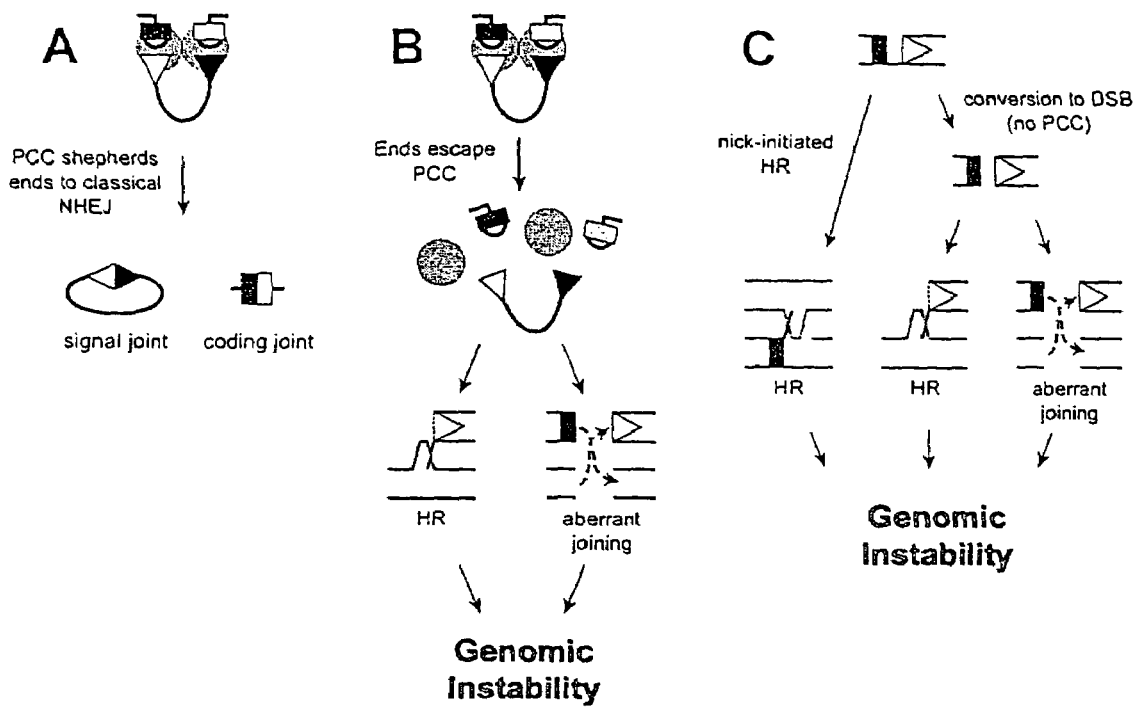
FIG. 8 illustrates models for RAG-mediated genomic instability. (A) In normal V(D)J recombination, the post-cleavage complex shepherds the broken DNA ends to the classical NHEJ repair pathway, protecting the genome from potentially dangerous aberrant recombination events. (B) If the broken DNA ends created during V(D)J recombination escape the post-cleavage complex, they become free to participate in homologous recombination with an ectopic partner after some end processing (indicated by a dotted line at the end of the RSS triangle) followed by crossing over (homologous recombination). Alternatively, the ends can join with a break on another chromosome created by aberrant joining, for example. The poorly characterized alternative NHEJ pathway is involved in such aberrant joining events and can promote chromosomal translocations. (C) RAG-generated nicks can also lead to genomic instability, either by initiating homologous recombination with an ectopic partner or through conversion to a double strand breaks that could then initiate homologous recombination or participate in other aberrant joining reactions. These double strand breaks might be particularly reactive, as they lack the protection of the RAG postcleavage complex. These models are not mutually exclusive.

The present invention provides methods for initiating homologous recombination One method utilizes RAG-generated nicks to initiate homologous recombination in mammalian cells. Another method stimulates homologous recombination from double-strand breaks using RAG mutants that stimulate hyper-homologous recombination by making the broken DNA ends more accessible for recombination than a standard nucleases such as I-SceI. The first method, stimulation of homologous recombination by introducing site-specific nicks, has the advantage of specifically stimulating homologous recombination without affording the opportunity for random integration through (double-strand) broken DNA ends. Thus, it is critical that nicks, and not DSBs, can stimulate homologous recombination. This has been demonstrated this via several independent lines of evidence (Lee et al., Cell, 2004) First, wild-type RAG proteins produce similar levels of homologous recombination on two types of substrates that yield different types of DNA ends: the CE substrate, which produces covalently sealed (hairpin) ends, and the SE substrate, which produces blunt ends. It is not expected that these two types of ends would give identical stimulation of homologous recombination since the hairpins must be opened before the ends can be available for recombination. This result would be expected, however, if nicks were the intermediate responsible for stimulating homologous recombination because both substrates are nicked equally. Second, nick-only RAG mutants (which efficiently make nicks but do not form double-strand breaks) stimulate homologous recombination as effectively as wild-type RAG proteins despite their inability to form detectable DSB. Third, wild-type RAG proteins produce similar levels of homologous recombination on both the SE substrate and the single RSS "nick-only" substrate, which does not support efficient DSB formation in vivo. Fourth, if RAG-mediated DSB were the initiating lesions, there should be a correlation levels of DSB and the level of homologous recombination. Yet, full-length RAG proteins, which generate far lower levels of signal ends than the truncated "core" proteins (Steen et al., MCB 1999) produce similar levels of homologous recombination on integrated substrates as core RAG proteins (FIGS. 4 and 7). Fifth, I-SceI generates fewer DSBs than the RAG proteins. Substantially more homologous recombination is observed with I-SceI than with wild-type RAG proteins (See, FIG. 3B) (we have identified RAG mutants, however, that stimulate far higher levels of homologous recombination than I-SceI, but give similar levels of DSB, suggesting that they are more efficient inducers of homologous recombination). Finally, while it could be thought that nicks could be converted to DSBs by some non-RAG mechanism such as DNA replication or nonspecific nuclease activity, two additional lines of evidence strongly argue against this possibility: 1) no DSB are detected by Southern blotting (Lee, Cell 2004) or by more sensitive ligation-mediated PCR (Huye Mol. Cell. Biol. 2002); and 2) if nicks were efficiently converted to DSB, coding or signal joints from nick-only mutants should be detected; but, they are not, either by sensitive PCR methods (Huye et al, Mol. Cell. Biol. 2002) or by fluorescent reporter assays (Lee and Roth, unpublished). Together these data provide proof that nicks can efficiently induce homologous recombination in mammalian cells.

As set forth herein, the present invention is based upon a nicking mechanism for creating nicks in a polynucleotide sequence. The nicking mechanism is preferably an enzyme capable of creating a nick in a polynucleotide sequence such as DNA. More preferably, the nick can be a. single-strand break or can be a break that leads to a double strand break. Regardless whether as nicks or as a nick-initiated double strand break, nicks efficiently stimulate homologous recombination. The nicking mechanism includes, but is not limited to, various recombinases such as a V(D)J recombinase, which consists of RAG-1 and RAG-2 proteins. The nicking mechanism can be in various forms including, but not limited to, naturally-occurring, wild-type, recombinant, mutant, and non-mutant. Nicking can be induced in living cells, which are the cells to be targeted, using an expression vector encoding the mutant recombinase. Alternatively, nicking can be induced outside of the cells by using mutant RAG recombinase proteins to nick purified DNA prior to its introduction into living cells (as is currently done with restriction enzymes to generate double-strand breaks prior to gene targeting). Preferably, the nicking can be a site-specific nick that results in more specific recombination. Moreover, the mutant forms of the nicking enzyme, such as mutant forms of RAG-1 or RAG-2, make nicks and not double strand breaks. Essentially, any nuclease that can create a site-specific nick can be used with the present invention. Examples of these nucleases include, but are not limited to, N.Alw, N.BstNB1, N.BbvC1A, N.BbvC1B, restriction endonucleases under certain conditions, viral and bacterial phage enzymes such as gene 2 F1, and enzymes that make non-specific nicks including, but not limited to, S1 nuclease, P1 nuclease, and mung bean nuclease.

Specifically, a nick in a polynucleotide stimulates homologous recombination as well as the double strand breaks produced by I-SceI. The remarkable efficiency with which a nick stimulates homologous recombination in this system argues against a mechanism requiring their conversion to a double strand break. The nicks are clearly not inert (as had previously been thought), and are not readily resealed by ligases (as had been widely believed ). Site-specific (or region-specific) nicks can also be intermediates in other recombination reactions such as immunoglobulin class-switching, somatic hypermutation, and immunoglobulin V (variable region) gene conversion.

The use of a nick can be advantageous in genetic engineering. Traditional methods for gene targeting via homologous recombination require the introduction of double strand breaks into the targeting vector to stimulate recombination. Although this tactic works, the DNA ends are also available for NHEJ, with the result being that non-targeted, random integrants typically predominate. Hence, the ability to introduce a site-specific nick into a substrate using nick-only RAG mutants preferentially stimulates locus-specific homologous recombination.

Support for the present invention is also based on the discovery that V(D)J recombinase can stimulate homologous recombination in mammalian cells. This is a surprising finding because, as is well known in the art, this recombinase does not normally participate in homologous recombination. Even more surprising, certain mutant forms of the recombinase that make only nicks instead of double strand breaks in the polynucleotide, also strongly stimulate homologous recombination. Because these RAG mutants do not create double strand breaks, but are still able to initiate homologous recombination, the mutants eliminate a major source of random integrations, which arise from the joining of broken DNA ends to a nonhomologous sequence.

Furthermore, in the unlikely event that nick-initiated homologous recombination can be a mechanism for the generation of oncogenic translocations, this is not expected to interfere with the potential for using nick-induced recombination for gene therapy or gene targeting, as the cells undergoing recombination express the nicking enzyme either transiently or not at all, and would be examined for undesirable genetic modifications prior to use in any therapeutic application. To remove all possibility of unwanted genomic modifications by the nicking enzyme, DNA is treated in the test tube with the enzyme and then the DNA is purified prior to its introduction into cells, as is commonly done in the case of DSB induced homologous recombination.

The finding that the RAG proteins can shepherd the broken DNA ends suggests that they reduce the undesired background events typically associated with gene targeting.

There are numerous embodiments of the present invention. In one embodiment, there is provided a method of stimulating homologous recombination utilizing the V(D)J recombinase (the RAG proteins) to create either nicks or double-strand DNA breaks (either in vivo or in vitro). In another embodiment, there is provided a method of stimulating homologous recombination by creating nicks in the polynucleotide using other enzymes (either in vivo or in vitro).

In one embodiment of the present invention, there is provided a method of using mutant RAG proteins, which are referred to as joining-deficient, to stimulate homologous recombination. These mutant RAG proteins hyper-stimulate homologous recombination as compared to a commonly used endonuclease, I-SceI, which does not stimulate homologous recombination as well because I-SceI enzymes are bound to at least one end (Perrin, et al.). This increased stimulation of homologous recombination is based on the finding that these mutant RAG proteins fall off the DNA after cleavage. Two RAG mutants have been shown to have this property and belong to a larger class of mutants. Thus, any nuclease that does not remain bound at the ends of the polynucleotide would stimulate homologous recombination. Moreover, any nuclease that would cleave DNA and rapidly dissociate thereof would work with the present invention. The mutant proteins can be expressed in vivo, where they would create site-specific breaks and fall off of the DNA, allowing rapid and efficient targeting. Additionally, these mutants could be used as purified proteins to create the breaks in vitro, on a purified DNA substrate in the test tube. These mutants are helpful in raising levels of gene targeting through the normal DSB-initiated pathway.

In another embodiment of the present invention, nick-only mutant RAG proteins or any other nucleases or proteins that generate nicks (such as those examples mentioned herein or other proteins that act in a similar manner) in DNA strands could be used to initiate homologous recombination. The proteins can be expressed in vivo, or could be used as purified proteins to create the nicks in vitro. In both instances, the use of nicks to initiate recombination is expected to increase the proportion of desired targeting effects by significantly reducing the undesired background events that arise through non-specific joining of double-strand breaks.

In yet another embodiment of the present invention, the mutant RAG proteins disclosed herein can be combined with nick-only mutations to create proteins or combination mutations that nick and then fall off of the target. This results in further increasing the availability of nicks to initiate recombination, while lowering the potential for the generation of undesirable background events through other repair pathways.

Figure 1:
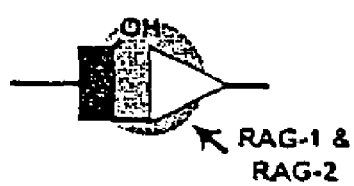
FIG. 1 illustrates V(D)J recombination. (1) The RAG proteins bind and create a single-strand nick at the border between the RSS (triangles) and coding sequence (boxes). (2) The RAG multimer must be bound to a pair of RSS, forming a synaptic complex, for the cleavage reaction to proceed. (3) The synaptic complex converts nicks to double-strand breaks via a transesterification reaction, generating blunt signal ends and hairpin coding ends (Roth, 2003), which are held in a post-cleavage complex by the RAG proteins. (4) After cleavage, the non-homologous end-joining (NHEJ) machinery ligates the signal ends to form a signal joint and opens and joins the hairpin coding ends to form a coding joint.
Figure 1:
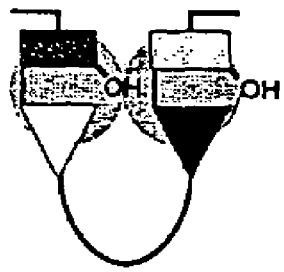
Figure 1:
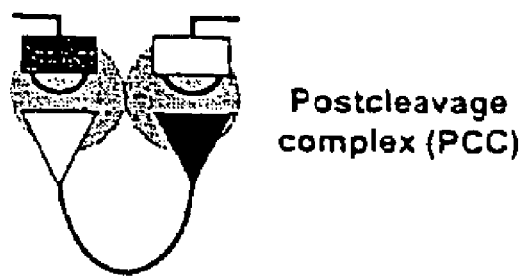
Figure 1:
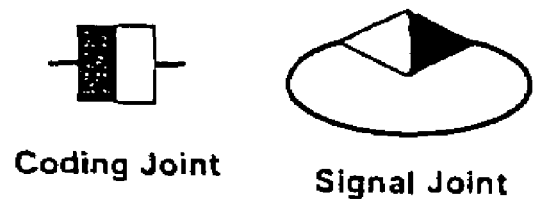

In other embodiments of the present invention, there are provided various kits. The kits include RAG mutants in either a purified form of the protein or as encoded in expression vectors, which make site-specific nicks or DSB at defined locations specified by the presence of signal sequences termed "recombination signal sequences." The kits enable quick and easy modification of cells by gene targeting with a greatly reduced background of non-targeted integration events. The mutant recombinases nick at the recombination signal sequences, which stimulates homologous recombination without generating a double-strand break. This avoids a major cause of random integration events, which, as noted above, are stimulated by double-strand breaks (See, FIG. 1). Alternatively, the kits can include other nucleases, either in a purified form, or as encoded in expression vectors. The general principle for kits utilizing these alternative nucleases is the same in that nicks or DSB would be generated in a site-specific manner, but use a different targeting sequence.

Figure 2:
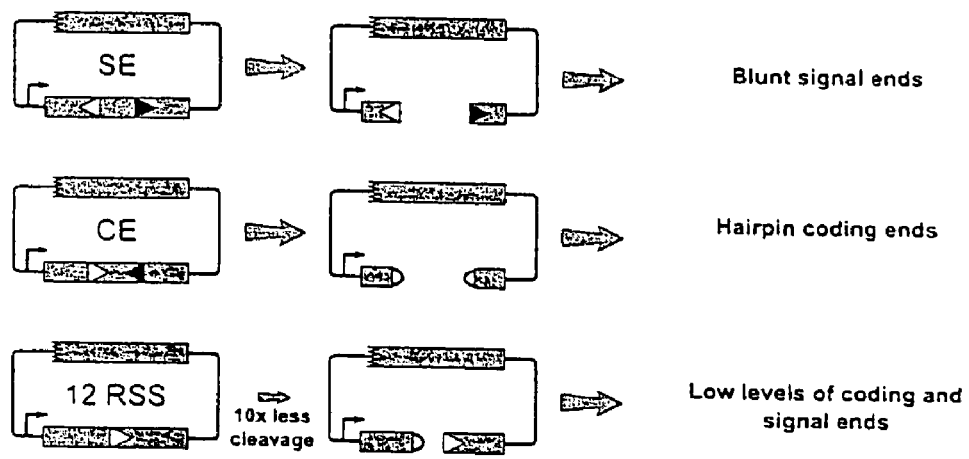
FIG. 2 illustrates a homologous recombination CFP assay. (A) Substrates employed to detect homologous recombination contain two defective alleles of the CFP gene and differ only in the inserted sequence used to target nucleolytic cleavage of one allele. One substrate contains RSS configured so that cleavage produces blunt signal ends (SE). In another substrate, cleavage produces hairpin coding ends (CE). A third substrate contains only a single RSS (12 RSS), which undergoes efficient nicking but poor DSB formation. (B) A site-specific DSB generated in one CFP allele by the RAG proteins can stimulate homology-directed repair using the nonfunctional (N-truncated) allele that produces a functional CFP gene. Truncated, core versions of murine RAG proteins are used unless otherwise noted.
Figure 2:
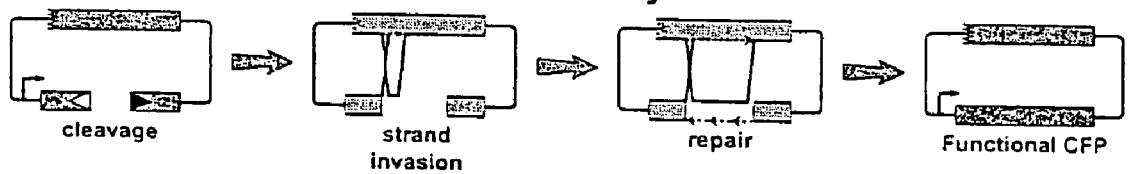

The kits of the present invention can include expression vectors. The expression vectors can be for "nick-only," "joining," or "combination" mutant RAG proteins (or other nucleases) to allow nicking of the target in transfected mammalian cells. Alternatively, the expression vector can be for a purified "nick-only" mutant Nucleases for nicking the target in the test tube, if desired. Further, a "targeting vector" that includes a selectable marker, as well as an RSS flanked by restriction sites, into which the user would subclone their homologous targeting sequence and the sequence to be inserted (FIG. 2) can be included in the kits of the present invention. Of course, any of the kits can include any one of these vectors or any combination thereof. The kit can also include any necessary reagents for the transfection of mammalian cells.

The targeting vector including the selectable marker can be in a variety of alternative forms. The kits of the present invention can include a "targeting oligonucleotide" (i.e., a recombination signal sequence to be used with RAG proteins, or a nuclease-specific recognition site, for use with other nucleases) that can be inserted into the region of homology, in order to target RAG-mediated nicking to a sequence if users desired to construct and use a specialized targeting vector. This oligonucleotide can terminate in sequences complementary to specific restriction sites to allow for easier subcloning. Yet another way in which a targeting sequence could be generated is through PCR amplification of the targeted region with primers containing the recognition site (either a recombination signal sequence or nuclease recognition sequence), followed by cloning of the products into a vector containing the sequence to be inserted and a selectable marker.

In another embodiment of the present invention, a component, mechanism, and method is disclosed for modulating and channeling site-specific DNA strand breaks to particular recombination pathways including, but not limited to, meiotic recombination, yeast mating type switching, somatic hypermutation, immunoglobulin class switching, and the like. In this embodiment, the post-cleavage complex is used to specify the pathway used to join the broken DNA intermediates. This embodiment is based on the discovery that RAG proteins form a recombinasome that sequesters the DNA ends, while shepherding them to the appropriate joining pathway. This mechanism ensures the fidelity of end joining by organizing the reaction so that the intermediates are carefully directed from one stage to the next in a protected complex. This shepherding function discourages entry into the low fidelity, nonclassical NHEJ pathway, which is a threat to genomic stability in lymphocytes. Thus, a healthy, post-cleavage complex prevents RAG-mediated DNA from proceeding to the nonclassical NHEJ pathway.

The discovery of a specific mechanism to guide DSBs into a particular repair pathway highlights the dynamic nature of the RAG post-cleavage complex. Without the RAG proteins directing DNA ends to the proper, high-fidelity joining pathway, the NHEJ factors, "genome guardians" though they can be, would not be able to serve their protective function, at least not in the context of V(D)J recombination. The shepherding activities of the V(D)J recombinase can provide a paradigm for repair of DSB in other contexts. Therefore, the present invention can be used in a variety of settings and for numerous applications.

For example, chromatin proteins can serve to restrict access of broken ends to the alternative NHEJ pathway. These shepherding complexes could be at work in other processes in which it would be advantageous to channel site-specific DNA strand breaks to particular repair pathways, such as meiotic recombination, yeast mating type switching, somatic hypermutation of immunoglobulin variable region genes, and immunoglobulin class switching. The present invention is useful as a screen for factors that affect various cellular recombination processes including, but not limited to, homologous recombination, immunoglobulin class switching, somatic hypermutation, immunoglobulin variable gene conversion, initiating oncogenic chromosomal rearrangements, and any similar recombination processes known to those of skill in the art. The present invention is also useful in channeling site-specific DNA strand breaks to particular recombination pathways, including, but not limited to, meiotic recombination, yeast mating type switching, somatic hypermutation, immunoglobulin class switching, and the like. The present invention is useful in gene therapy, gene targeting, generation of gene knockouts, and other related therapeutic methods.

The present invention can be used to improve the efficiency of gene targeting in a variety of systems. As a result, the present invention brings mammalian systems closer to the efficiency of homologous recombination obtained routinely in yeast. Thus, more specific applications include the use of the present invention with targeted embryonic stem cells. Increased gene targeting efficiency in embryonic stem cells provide a powerful tool for creating chimeric mice (or other animals), one of the most powerful tools available in the analysis of gene function. A large increase in the ability to manipulate the genome in this fashion increases the rate at which such studies could be completed, and can make the technology available to smaller labs to which it might have been previously unavailable.

The present invention can also be used with targeted stem cells. The present invention greatly simplifies targeting of stem cells, including human stem cells, for both research and therapeutic purposes. For example, adult muscle stem cells from a patient suffering from muscular dystrophy are isolated and a functional dystrophin gene targeted to replace the mutant allele. These stem cells are then used to rehabilitate the patient. Many genetic diseases could be approached by this technique, treating cells ex vivo and then re-introducing them into the patient. Obvious candidates include, but are not limited to, various varieties of inherited severe combined immunodeficiency (SCID). By substantially increasing the efficiency of targeting, ex vivo gene correction strategies in stem cells bearing the mutant genes can become a viable therapeutic alternative.

In yet another application, the present invention can be used for gene targeting in somatic cells. Targeting expression or treatment of the recombinase can occur inside the cells or by treating naked DNA outside the cell. Nicking can occur inside the cell or outside the cell. The efficiency of gene targeting in mammalian somatic cells is notoriously low, and the technique is almost never practiced in these cells. Analyses of gene function in living cells can be tremendously aided if there was an efficient method for generating knockouts and targeted mutations (knock-ins) in somatic cells, especially cell lines in tissue culture.

Additionally, the present invention can be used in re-targeting genomic loci for analysis of gene function. Insertional mutagenesis is a common method for generating mutant alleles, and therefore identifying genes associated with particular phenotypes. Introduction of an RSS into the insertional mutagenesis vector (typically, a retrovirus) allow for rapid targeting of the locus upon transfection of the mutant RAG proteins and introduction of a targeting vector bearing appropriate homologous sequences. This facilitates detailed analyses of gene function.

The above discussion provides a factual basis for the use of the present invention described herein. The methods used with a utility of the present invention can be shown by the following non-limiting examples and accompanying figures.

EXAMPLES

Materials and Methods for Examples

General Methods in Molecular Biology:
Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series*, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

Recombinant Protein Purification:
Marshak et al, "Strategies for Protein Purification and Characterization. A laboratory course manual." CSHL Press, 1996.

Transgenic and Knockout Methods:
The present invention can provide for transgenic gene and polymorphic gene animal and cellular (cell lines) models as well as for knockout models. These models are constructed using standard methods known in the art and as set forth in U.S. Pat Nos. 5,487,992, 5,464,764, 5,387,742, 5,360,735, 5,347,075, 5,298,422, 5,288,846, 5,221,778, 5,175,385, 5,175,384,5,175,383, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

For Gene Therapy:
The present invention can be used for gene therapy wherein a DNA vector is treated with a nick-only mutant (or another nicking nuclease) in the test tube, then it is introduced into the desired cells by standard transfection techniques. Alternatively, living cells can be treated ex vivo with nick-only mutants transfected into the cells (to nick a co-introduced plasmid vector that includes a site for the nuclease). Furthermore, living cells can be treated in vivo with a viral vector encoding such a mutant.

By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. Alternatively, the genetic material of interest encodes a suicide gene. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ that is within the recipient. In an alternative embodiment, if the host gene is defective, the gene is repaired in situ [Culver, 1998]. These genetically altered cells have been shown to express the transfected genetic material in situ.

The gene expression vehicle is capable of delivery/transfer of heterologous nucleic acid into a host cell. The expression vehicle can include elements to control targeting, expression and transcription of the nucleic acid in a cell selective manner as is known in the art. It should be noted that often the 5'UTR and/or 3'UTR of the gene might be replaced by the 5'UTR and/or 3'UTR of the expression vehicle. Therefore as used herein the expression vehicle can, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that can be required to obtain necessary transcription levels can optionally be included. Enhancers are generally any non-translated DNA sequence, which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature.

Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor, which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer were to be treated then a vector specific for such epithelial cells would be used. Likewise, if diseases or pathological conditions of the hematopoietic system were to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles, which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. One skilled within the art knows such transfection vehicles.

Generation of Substrates:

An insertion containing a BglII site and an EcoRV site is generated in the center of the enhanced cyan-fluorescent protein (eCFP) gene of the pECFP-N1 vector (Clontech). A N-terminally truncated eCFP gene is generated by PCR and cloned into the BsaI site of this vector, generating a plasmid (pECFP-int-NtCFP) containing both an interrupted eCFP gene (eCFP-int), and an N-terminally truncated eCFP gene (NtCFP). Several different sequences are then cloned into the BglII-EcoRV fragment of the interrupted eCFP gene, yielding the I-SceI substrate (I-SceI site inserted), the 12 substrate (12 RSS of sequence 5'-CACAGTGCTACAGACTGGM-CAAAAACC-3' inserted) (SEQ ID NO. 1), the SE substrate (PCR-generated fragment of pJH289 recombination zone inserted (Hesse et al., 1987)), and the CE substrate (PCR-generated fragment of pJH290 recombination zone inserted (Hesse et al., 1987)).

Figure 9:
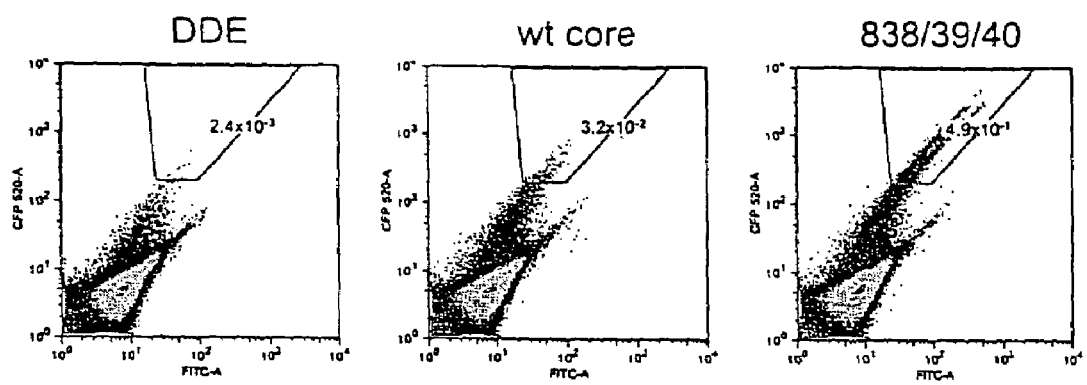
FIG. 9 provides for examples of data obtained by flow cytometry using extrachromosomal substrates. Cells are prepared as described in Examples Section. In order to exclude background events, gates are used to exclude the majority of events seen in the negative controls. 500,000 total events are observed for each condition. On average, approximately 90% of the cells are determined to be live cells by forward and side scatter and are analyzed further. In the DDE mutant-containing transfection, 11 events are observed (0.00239%), and in the wt core RAG-containing transfection, 145 events are observed (0.032%), resulting in a stimulation of about 13-fold ((0.032)/(0.00239)). In the 838/39/40-containing transfection, 1980 events are observed (0.49%), resulting in a stimulation of about 205-fold ((0.49)/(0.00239)) over DDE, and about 15-fold ((0.49)/(0.032)) over wild-type core. Numbers indicate percentage of live cells falling within the indicated gate. Colors represent cell density, with red denoting the highest and blue the lowest densities.
Figure 10:
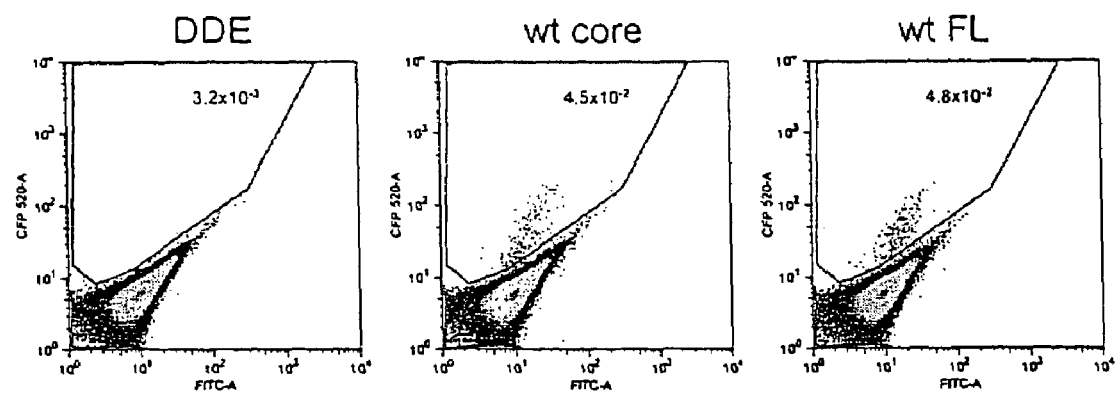
FIG. 10 provide for examples of data obtained by flow cytometry using cell lines containing integrated substrates. Cells are prepared as described in the Examples Section. In order to exclude background events, gates are set to exclude the majority of events seen in the negative controls. The background events (cells that are above the diagonal but below the positive gate in the DDE-containing transfection (See, FIG. 9)) are greatly reduced when using integrated substrates. In the experiments shown, 500,000 total events are observed for each condition. Approximately 90% of cells are determined to be live cells by forward and side scatter, and are further analyzed. In the DDE mutant-containing transfection, 15 events are observed (0.0032%), and in the wt core RAG-containing transfection, 211 events are observed (0.045%), resulting in a stimulation of about 14-fold ((0.045)/(0.0032)). In the full-length RAG-containing transfection, 217 events were observed (0.048%), resulting in a stimulation of (0.048)/(0.0032)=15-fold over the DDE mutant.

Flow Cytometry:

Cells are trypsinized 50-60 hours post-transfection and re-suspended in 0.5 mL complete DMEM containing 10% FBS. Samples are run on a Becton Dickinson LSRII, using FACSDiVa software (version 3.0). Samples are gated to include only live cells, and 500,000 events are analyzed for each transfection. The proportion of live cells is not affected by any of the RAG mutants. Analysis compared CFP signal, which was excited using a 405 nm laser and detected through 525/50 bandpass and 505 longpass filters, to a FITC (fluorescein isothiocyanate) signal, which was excited using a 488 nm laser and detected through 530/30 bandpass and 505 longpass filters. This method allows for distinguishing CFP-positive cells from cells displaying autofluorescence (autofluorescent cells fluoresce equally brightly at both wavelengths, forming a diagonal) (See, FIGS. 9 and 10) (Pierce et al., 1999). Gates are drawn to exclude most events present in the DDE-containing transfections, which are considered to be background events this rationale is supported by the finding that these events are also present when substrates lacking an RSS sequence are used. These background events are much more prevalent in the extrachromosomal assay than in the assays using integrated substrates, allowing the gates to be more inclusive in the transfections using integrated substrates (See, FIGS. 9 and 10). These more inclusive gates allowed detection of stimulation by full-length RAG proteins using integrated substrates. Relative stimulation is calculated by dividing the percentage of CFP-positive cells of experimental (nuclease-containing) transfections by the percentage of CFP-positive cells present in the DDE RAG mutant expressing transfection (negative control). It is important to maintain constant (DNA) in each transfection because increases in DNA (including non-substrate molecules) nonspecifically stimulate homologous recombination, as recently reported (Hostager et al., 2003). Experiments have been repeated over a dozen times on three different flow cytometers; FIGS. 3, 4, 6, and 7 show data from five experiments on the Becton Dickinson LSRII.

Generation of Integrated Substrates:

RMP41 fibroblasts were grown to 50% confluency. Substrates (μg) are digested with ApaLI, which linearized the plasmids. The plasmids are then phenol-chloroform extracted, precipitated, and resuspended in 20 μl of Tris-EDTA (pH 8). Substrates are then transfected using a mix of 250 μl serum-free DMEM and 8 μl Fugene. Twelve to eighteen hours later, cells are trypsinized, resuspended, and plated at several dilutions. Medium is changed every three days and included Geneticin at a concentration of 1.5 mg/mL. After 10-14 days, single colonies are picked and grown in 96 well plates. Upon growing to confluency, clonal cultures are split and tested for activity by flow cytometry and fluorescence microscopy as described above.

Thermal Stability of Post-Cleavage Signal End Complex

GST-tagged truncated RAG proteins are purified from RMP41 fibroblasts by GST affinity chromatography (Huye et al., 2002). For RAG-mediated cleavage, 100 ng of the recombination substrate pJH290 is incubated for three hours at 37° C. with 200 ng of purified RAG protein and 200 ng of purified recombinant HMG (Huye et al., 2002) in a buffer containing 50 mM HEPES pH8.0, 25 mM, 4 mM NaCl, 1 mM DTT, 0.1 mg BSA, 5 mM CaCl, and 5 mM MgCl2. Reactions are then incubated at different temperatures for thirty minutes and treated with T4 ligase overnight at room temperature in the absence of PEG. PCR and Southern blotting to detect signal joints are performed as previously described (Huye et al., 2002). The control PCR product is amplified using the primers NSfor (5'-CAGTTAATMCAGAAAATAAGCCAGGCC-3') (SEQ ID NO: 2) and NSrev (5'-CAMATCAAGATMTAC-CCCATAATTMCAGG-3') (SEQ ID NO: 3).

Cell Culture:

RMP41 fibroblasts are grown in DMEM (Invitrogen) supplemented with fetal bovine serum (10%), non-essential amino acids, and penicillin-streptomycin. Cells are grown at 37° C. in the presence of 5% $CO_2$. Cells containing integrated substrates are selected and grown in the presence of 1.5 mg/mL Geneticin (Gibco).

Protein Expression:

Truncated RAG proteins are expressed in the pEBG-1DN vector (RAG-1) (Spanopoulou et al., 1996) and the pMal-1 vector (RAG-2)(Landree et al., 1999). The I-SceI homing endonucleases, is expressed in the pCMV-ISceI vector (Rouet et al., 1994). Mutations in the core RAG genes producing a nick-only or joining-deficient phenotype are indicated by residue number and have been previously characterized (Huye et al., 2002; Qiu et al., 2001; Yarnall Schultz et al., 2001). The DDE mutant (D600A/D708A/E962A) is a catalytically dead RAG-1 mutant used as a control (Landree et al., 1999).

Figure 11:
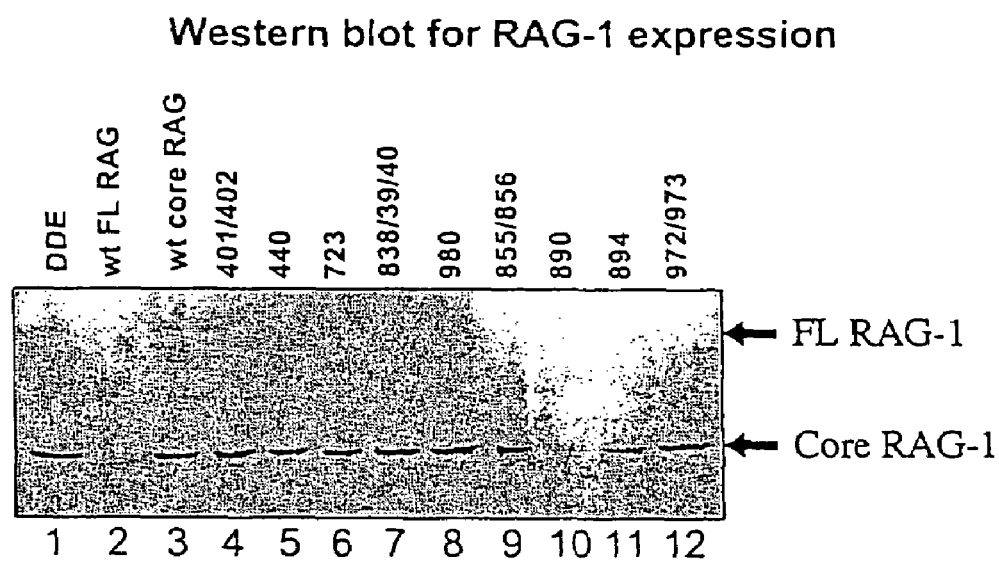
FIG. 11 illustrates expression of mutant RAG-1 proteins. In order to further verify that the differences seen in stimulation of homologous recombination by the mutant RAG proteins are not due to variations in protein expression, western blots against the GST affinity tag present as a fusion on the RAG proteins are performed. A representative blot is shown. Expected sizes for the RAG proteins are indicated by arrows.
Figure 12:
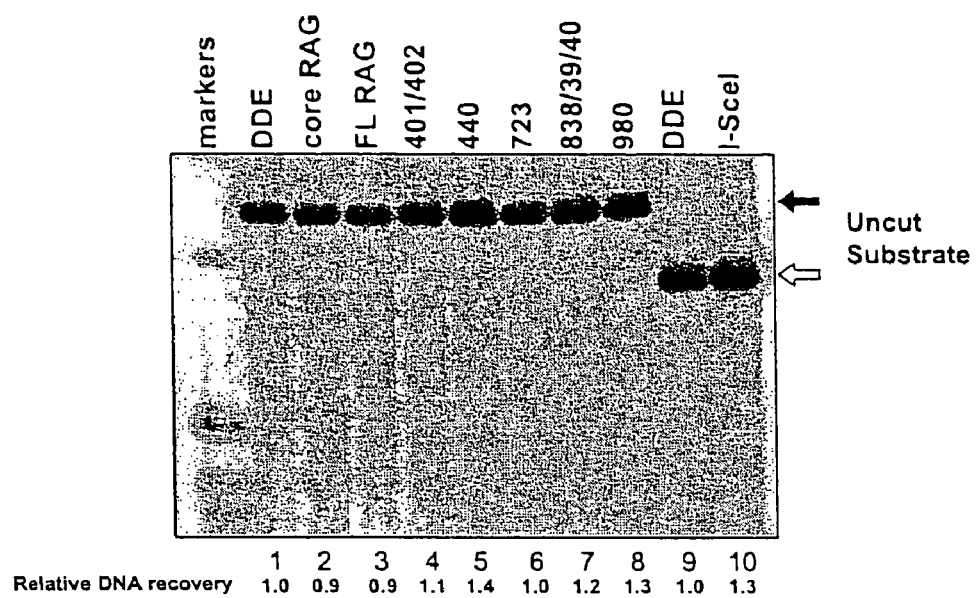
FIG. 12 illustrates DNA recovery from Hirt preps. Relative recoveries of uncut substrate are shown in order to compare DNA recovery between samples. Lanes 1-8 are normalized to recovery in lane 1, while lanes 9 and 10 are normalized to recovery in lane 9 because they contain a differently-sized uncut substrate.
Figure 14:
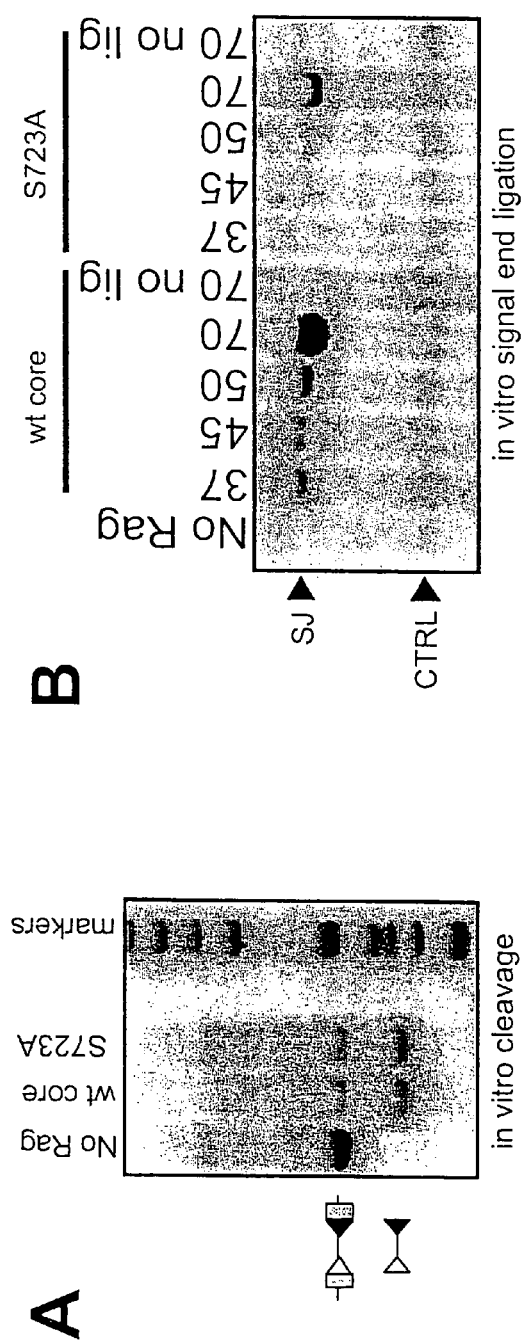
FIG. 14 illustrates (A) a Gel comparing in vitro cleavage of a $^{32}$P body-labeled substrate by wild-type and S723A core RAG-1 proteins. The substrate is a PCR product amplified from the relevant region of the recombination substrate pJH290. Uncleaved substrate (478 nt) and cleaved signal end product (329 nt) are indicated by pictograms to the left of the gel. Approximately 200 ng each of core RAG-1 and core RAG-2 are incubated at 37° C. in a cleavage mixture containing 50 mM HEPES (pH 8.0), 26 mM KCl, 4 mM NaCl, 1 mM DTT, 5 mM CaCl$_2$, 1 µg/µl BSA, 200 ng HMG, and substrate. After 15 minutes, MgCl$_2$ was added to a final concentration of 5 mM. Reactions are terminated by adding 0.2 volume of stop buffer (100 mM tris (pH 8.0), 10 mM EDTA, 0.2% SDS, 0.35 µg/µl proteinase K) and incubating at 55° C. for 30 minutes. (B) In vitro recircularization assay for signal end release is shown. Unlike R838A/K839A/R840A and K980A, the S723A mutant RAG-1 did not show greater signal end release than the wild-type protein. Experiments are performed as set forth in FIG. 5 and the Examples Section. (C) Results shown in B are analyzed as described previously in FIG. 5, wherein the graph shows the percentage of maximal release of signal ends by S723A and wild-type RAG-1.
Figure 14:
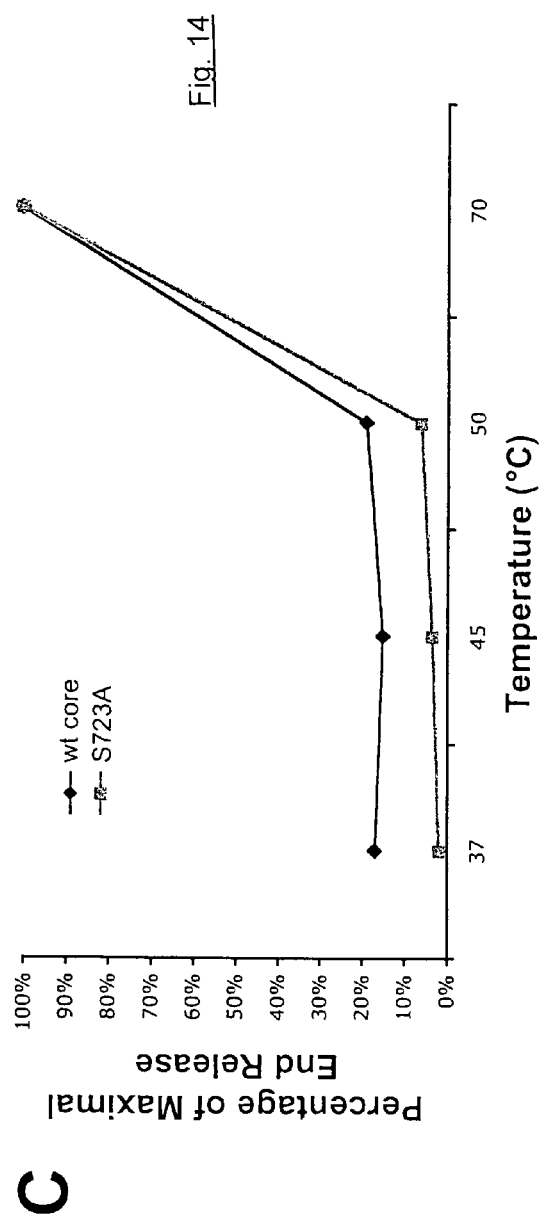

Transient Transfections:

CHO (RMP41) fibroblasts are grown to 50% confluency in 96-well plates (Corning). Transfections are done in groups of 8 wells that are pooled upon harvesting. Each transfection contains 800 ng of each plasmid (substrate as indicated, and either I-SceI or RAG expression vectors as indicated), 240 µl of serum-free DMEM, and 4 µl of Fugene transfection reagent (Roche). When using cell lines containing integrated substrates, substrate plasmids are omitted, and Fugene is reduced to 3 µl. As measures of consistent transfection efficiency, the following is shown: 1) error bars show the data to be highly reproducible; 2) Western blots show consistent expression of RAG mutant proteins (FIG. 11); 3) recovery of transfected substrate DNA is consistent (FIG. 12).

Fluorescence Microscopy:

Forty-eight hours after transfection, cells are trypsinized, re-suspended, and placed in Lab-Tek II 4-chambered slides (Nalge Nunc International). Cells are visualized using a Leica DMIRB inverted fluorescence microscope. Pictures are taken using an Axiocam HR and Axiovision software (Zeiss).

Southern Blots:

DNA is prepared from cells by the Hirt method previously used and disclosed (Steen et al., 1996). DNA is digested using HpaI and NcoI for two hours, then run on a 2% native agarose gel. DNA is transferred to Genescreen membrane using a posiblotter (Stratagene). The DNA is then crosslinked to the membrane by UV irradiation. Probes are generated with a random priming DNA labeling kit (Gibco) using a gel-purified HpaI-NcoI fragment from the pECFP-int vector as a template. Probes are hybridized to blots overnight at 65° C. in a solution of 10% Dextran Sulfate, 1 M NaCl and 1% SDS. Blots are visualized using a Phosphorimager and ImageQuant Software (Molecular Dynamics).

Example One

Unstable Post-cleavage Complexes Stimulate Homologous Recombination

The joining step of V(D)J recombination could be impaired by any of several distinct mechanistic defects, such as an unstable post-cleavage complex that releases ends prematurely, hyper-stability (i.e., the complex retains the ends too avidly), or failure to recruit joining factors (Qiu et al., 2001; Yarnall Schultz et al., 2001; Brandt and Roth, 2002; Huye et al., 2002). Therefore, after establishing baseline levels of homologous recombination observed with wild-type core RAG proteins, the CFP assay was used to test 15 mutants (six in RAG-1 and nine in RAG-2; See, FIG. 13) that can perform cleavage, but are severely impaired in the joining phase of recombination (Huye et al., 2002; Qiu et al., 2001; Yarnall Schultz et al., 2001). The RAG-1 mutant, S723A, was tested. This mutant was reported to have a joining defect (Tsai et al., 2002). All of these mutants are expressed at wild-type levels in vivo (See, FIG. 11) and most have a mild cleavage defect (See, FIG. 12 and Huye et al., 2002, Qiu et al., 2001, and Yarnall Schultz et al., 2001). With regard to FIG. 11, the full-length RAG proteins are expressed at a level much lower than their core counterparts, which is an observation that has been previously reported (Steen et al., 1999). The various core RAG proteins are all expressed at similar levels, with the exception of K890A, a nick-only mutant. Notwithstanding the lower level of expression, this mutant catalyzed robust homologous recombination (See, FIGS. 6 and 7). Protein pellets are isolated from transient transfections and resuspended in 200 ml of 0.1% SDS and resolved on an 8% SDS-PAGE gel. Proteins are transferred to a PVDF membrane (Biorad). Blocking is performed in TBST+5% nonfat dry milk overnight at 4° C. Primary antibody (a-GST mouse IgG1) is bound at a 1:1000 dilution for one hour at room temperature. Secondary antibody (from ECF mouse western kit, Amersham) is bound at a 1:10000 dilution for 1 hour at room temperature. ECF reagent is applied for two minutes and the blot is scanned using a phosphorimager (Molecular Dynamics).

Two of the sixteen mutants, RAG-1 K980A and RAG-1 R838A/K839A/R840A, stimulate robust homologous recombination compared to wild-type RAG controls, as seen by fluorescence microscopy (FIG. 3A). Flow cytometry confirmed dramatic stimulation. Both mutants consistently produced 10-15 times as much homologous recombination as wild-type core RAG controls (the relevant control, since the mutants are on a core background) ($p<0.000008$, FIG. 3B). The RAG-1 R838A/K839A/R840A mutant was also tested with the signal end substrate integrated into the CHO genome. This mutant consistently generated higher levels of homologous recombination than wild-type core RAG-1 controls ($p<0.0004$, FIG. 4). The ability of these two mutants to stimulate homologous recombination is even more impressive in light of their mild cleavage defect in vivo: R838A/K839A/R840A and K980A produce 2.5-fold lower levels of signal ends in vivo than wild-type RAG proteins (FIG. 3C and FIG. 12). Thus, on a per-end basis, these mutants stimulate ~25 to 35 times more homologous recombination than wild-type RAG proteins.

The high levels of homologous recombination produced by the two joining-deficient mutants are not observed with a coding-end substrate, and are therefore specific for signal ends (FIG. 3B, right side of graph). This indicates that covalently sealed coding ends do not trigger homologous recombination.

Figure 3:
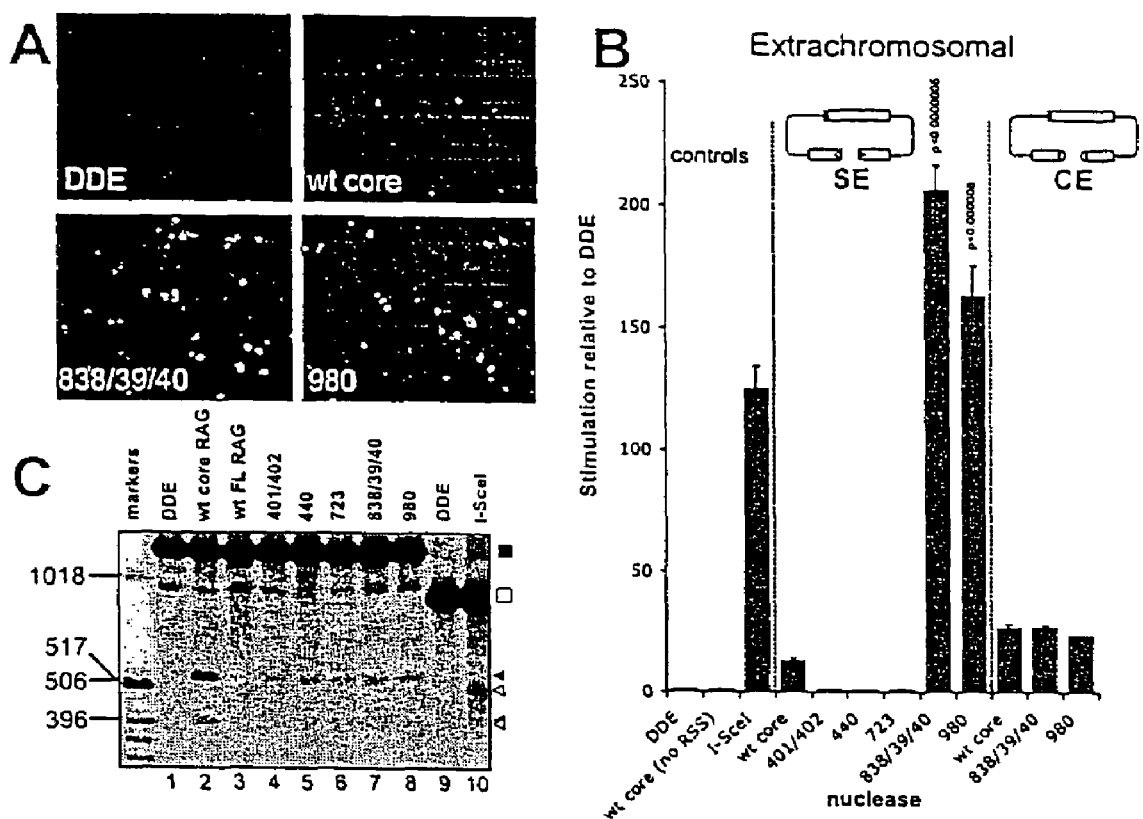
FIG. 3 illustrates two RAG mutants that stimulate robust homologous recombination on extrachromosomal substrates. (A) Fluorescent images of cells showing stimulation of homologous recombination by wild-type and joining-deficient RAG proteins (original magnification 100×). (B) Relative stimulation of CFP expression by wild-type and joining-deficient RAG-1 proteins (R401A/R402A, R440A, S723A, R838A/K839A/R840A, K980A) quantitated by flow cytometry (See, Methods in Example Section and FIGS. 9-14). Error bars here and elsewhere represent standard error of the mean (S.E.M.) from at least five experiments. (C) Southern blot of DNA from transfections showing the levels of cleavage by wild-type and joining-deficient RAG proteins. DNA recovered from transfections by the Hirt method are digested with HpaI and NcoI and analyzed by Southern blotting. Expected fragment sizes of the SE substrate: uncleaved, 1229 bp (filled square); cleavage products, 557 and 416 bp (filled arrowheads). Expected fragment sizes of the I-SceI substrate: uncleaved, 903 bp (open square); cleavage products, 509 and 394 (open arrowheads). All mutant proteins show decreased cleavage. The uncleaved substrate bands (squares) serve as an internal control for relative transfection efficiencies and DNA recoveries between samples. Average DNA recovery varied less than 10% by phosphorimager quantitation (See, FIG. 12).
Figure 4:
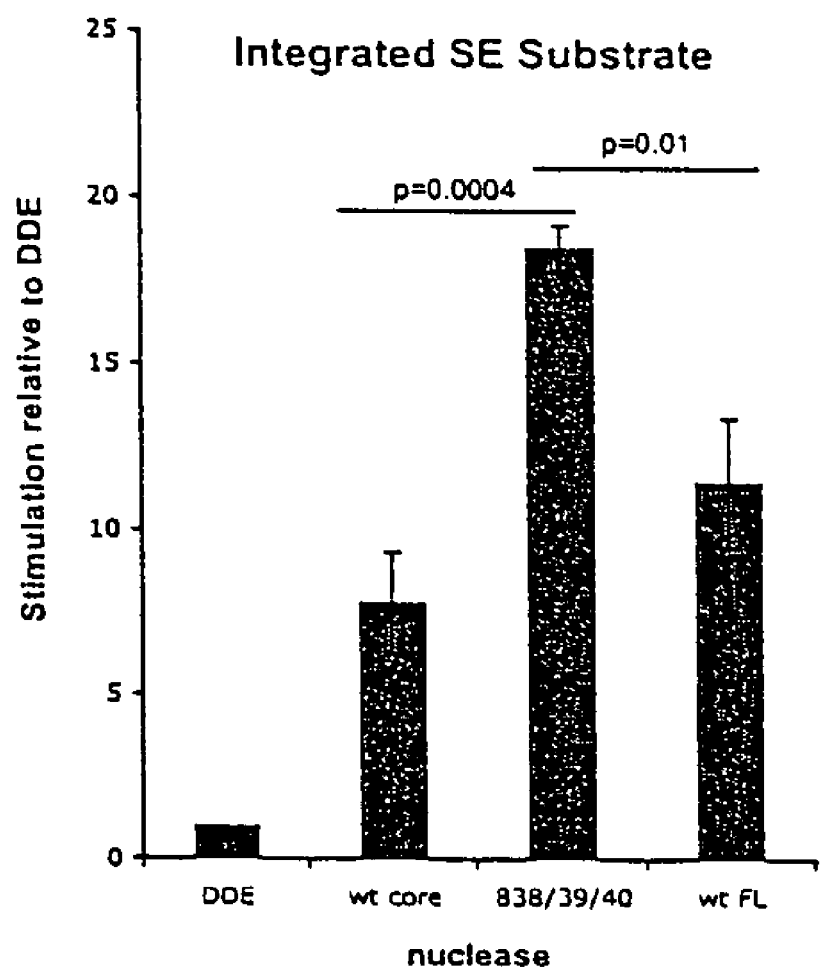
FIG. 4 illustrates that RAG mutants stimulate homologous recombination on an integrated substrate. As shown, the joining-deficient RAG-1 protein, R838A/K839A/R840A, stimulated more homologous recombination than the wild-type RAG proteins ($p<0.0004$, $p<0.01$ for core and full-length, respectively) in a cell line with an integrated SE substrate. Further, two independent cell lines gave similar results.

The data shown in FIGS. 3 and 4 suggest that these two RAG-1 joining mutants form unstable post-cleavage complexes that fail to shepherd signal end intermediates to NHEJ, leaving the free signal ends to initiate homologous repair. These results prove that the wild-type RAG proteins (both core and full-length versions) prevent the signal ends from accessing the homologous recombination machinery. A comparison with results obtained from I-SceI supports the conclusion that whereas I-SceI generates fewer broken ends (~2.5-fold less) than wild-type core RAG proteins (FIG. 3C), I-SceI stimulates homologous recombination ~9 times better (FIG. 3B). Thus, the (fewer) I-SceI-generated ends are far more readily available to the homologous recombination machinery than ends produced by wild-type RAG proteins—at least 20-fold on a per-end basis. The situation is reversed with the RAG-1 K980A and RAG-1 R838A/K839A/R840A mutants, which produce virtually the same levels of broken ends as I-SceI (FIG. 3C). These mutants stimulate significantly higher levels of homologous recombination than I-SceI (FIG. 3, $p<0.05$ and $p<0.0007$, respectively).

In vitro work shows that after cleavage by I-SceI, only one DNA end remains associated with the enzyme (Perrin et al., 1993). The explanation for these data is that the RAG post-cleavage complex affords the greatest sequestration of DNA ends. Further, I-SceI restricts the accessibility of ends to some degree (retaining one); and the two unstable RAG mutants fail to retain the DNA ends at all. The fact that the mutants stimulate roughly twice as much homologous recombination as I-SceI, which retains only one set of ends, dovetails nicely with this explanation. To test the hypothesis that the two joining-deficient RAG mutants prematurely release the signal ends in vivo, the stability of the mutant post-cleavage complexes in vitro is examined.

After cleavage in vitro, purified RAG proteins remain tightly bound to the signal ends. Disruption of this association requires harsh treatments, such as phenol extraction or heating to high temperatures (70° C.) (Jones and Gellert, 2001; Leu et al., 1997; Ramsden et al., 1997), which presumably denature the bound RAG proteins. Capitalizing on previous work showing that the signal ends become available for joining by ligase only after the RAG proteins are removed (for example, by incubation at 70° C.) (Jones and Gellert, 2001; Leu et al., 1997; Ramsden et al., 1997), the post-cleavage complex stability was assessed in a straightforward manner, wherein RAG cleavage occurs and incubation of the reactions occurred at a series of temperatures ranging from 37 to 70° C. to allow disruption of the post-cleavage complex. Then, measured levels of signal end ligation (schematized in FIG. 5A) took place. As expected, wild-type post-cleavage complexes do not release significant proportions of the signal ends at 37, 45, or 50° C. Only at 70° C. does quantitative end release occur, as measured by the ability of the two ends to be ligated (See, FIG. 5B)(Quantitative end release by treatment at 70° C. was verified in other experiments by comparison to treatment with SDS/proteinase K. Wild-type RAG proteins showed little end release below 70° C., whereas joining-deficient mutant RAG proteins showed maximal levels of end release even at the lowest temperature tested. As expected, the modest cleavage defect of the mutant RAG proteins (See, FIG. 3C) resulted in 10-fold lower levels of signal ends overall than wild-type (Huye et al., 2002).).

Figure 5:
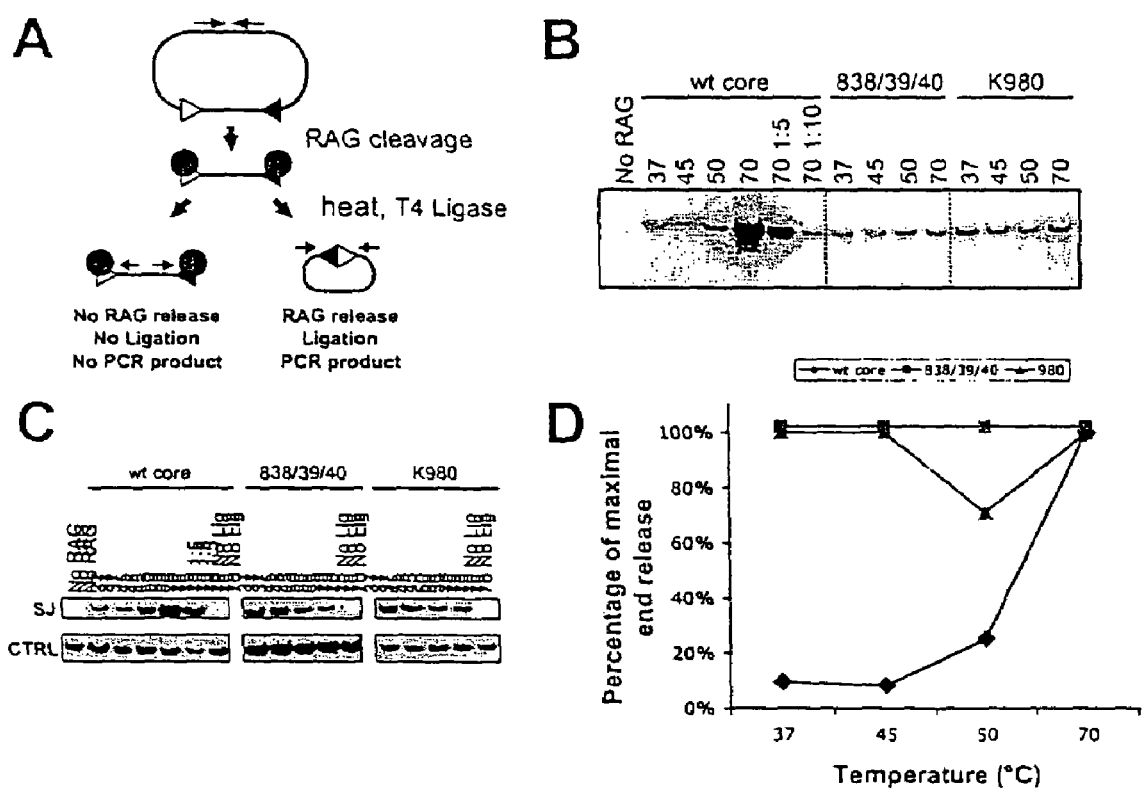
FIG. 5 illustrates joining-deficient RAG mutants from an unstable post-cleavage complex. (A) A plasmid recombination substrate (pJH290) is subjected to in vitro cleavage reactions using purified RAG proteins. After cleavage, reactions are treated at various temperatures to measure the stability of RAG post-cleavage complex binding to the signal ends (See Methods of Example Section). Signal end release allows ligation and generation of a PCR product. (B) Southern blot showing signal end release by the RAG proteins as measured by the availability of ends for ligation. (C) Southern blot (from a second experiment using a different protein prep) showing signal end release by the RAG proteins (SJ). (D) Graph showing the percentage of maximal release of signal ends. Amounts of signal joint PCR product (SJ) in each lane were normalized according to the amount of control PCR product (CTRL). Percentage of maximal release was calculated as the intensity of each band over the intensity of the band generated by treatment at 70° C.
Figure 6:
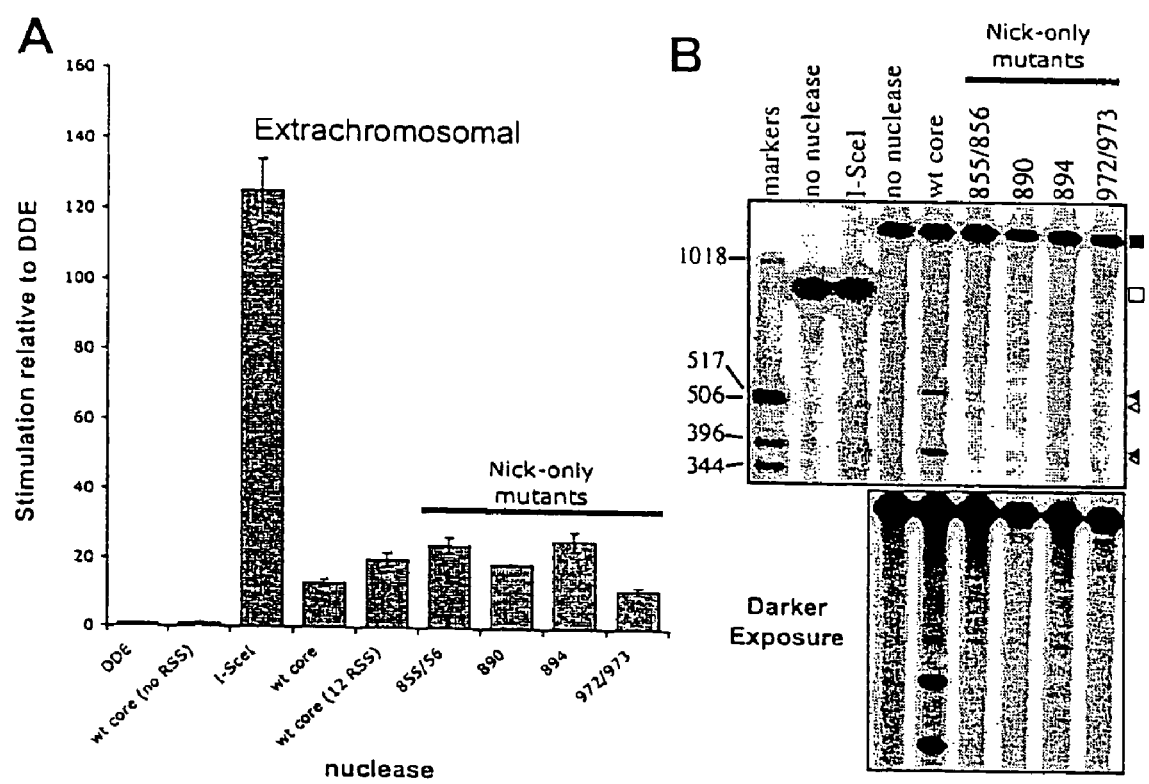
FIG. 6 illustrates RAG-generated nicks stimulate homologous recombination on extrachromosomal substrate. (A) Graph showing relative stimulation of CFP expression by wild-type core and nick-only mutant RAG-1 proteins (R855A/K856A, K890A, R894A, and R972A/K973A) on SE substrate, unless otherwise noted. (B) Southern blot of HpaI- and NcoI-digested DNA recovered from cells expressing wild-type core and the same nick-only mutant RAG proteins. Cleavage products are described in FIG. 2D.

In sharp contrast, post-cleavage complexes formed by K980A or R838A/K839A/R840A showed maximal release of the signal ends even at the lowest temperature tested, 37° C. (FIG. 5B). Repeating this experiment with different protein preparations and added a loading control (a second set of PCR primers that amplifies a short segment from the plasmid backbone) obtained the same results (See, FIG. 5C). As in panel (B), wild-type RAG proteins showed little end release below 70° C., whereas joining-deficient mutants showed maximal end release even at the lowest temperature tested. The non-specific control PCR products (CTRL) indicate that differences observed were not due to fluctuations in amounts of template or gel loading.

Because the mutant RAG proteins have a ~5-10-fold cleavage defect in vitro ((Huye et al., 2002) and data not shown), they produce fewer ligatable ends than wild-type RAG proteins, which is reflected in the data. Data from the experiment shown in FIG. 5C are quantitated in FIG. 5D. The convergence of the results from the CFP in vivo assay and end release in vitro lead to the conclusion that these two mutants form unstable post-cleavage complexes that fail to properly retain the signal ends.

None of the other 13 joining-deficient RAG-1 and RAG-2 mutants stimulated homologous recombination better than wild-type RAG proteins (FIG. 3B and data not shown). Indeed, many actually yielded lower levels of homologous recombination than wild-type RAG proteins. This is the case with the S723A mutant, which had been reported to display a mild tendency to release signal ends in vitro (Tsai et al., 2002). This evidence indicates that this RAG-1 mutant, like most of our joining-deficient RAG mutants, does not increase the accessibility of the signal ends to other recombination pathways in living cells.

Example Two

The Post-cleavage Complex Protects Ends From Alternative NHEJ

Cells and extracts deficient for classical NHEJ components (Ku, XRCC4, etc,) (Baumann and West, 1998; Kabotyanski et al., 1998; Roth, 2002; Verkaik et al., 2002) are still able to perform end joining very efficiently, enough to allow cell survival by virtue of an ill-defined pathway known as "alternative NHEJ" (Roth, 2003). The factors that participate in alternative NHEJ are not known, but junctions formed by this repair pathway characteristically display excessive deletions and reliance on short sequence homologies (microhomologies) (Roth and Wilson, 1986). Alternative NHEJ is also quite error-prone and has been implicated in spontaneous and V(D)J recombination-induced chromosome aberrations that display the hallmark microhomologies (Ferguson et al., 2000; Zhu et al., 2002). Considering the dangers inherent in using a translocation-prone mechanism for joining V(D)J recombination intermediates, it is prudent for the post-cleavage complex to sequester the ends from this pathway. Indeed, this is the case wherein the efficiency of end joining of transfected linear plasmid substrates is virtually unaffected in Ku80- and XRCC4-deficient cell lines (Kabotyanski et al., 1998; Verkaik et al., 2002), joining of ends generated by RAG-mediated cleavage of essentially the same plasmid substrates is decreased more than a hundred-fold (Han et al., 1998; Han et al., 1997; Taccioli et al., 1993). This result had been quite puzzling, but the present data suggest a plausible explanation: the post-cleavage complex prevents RAG-generated breaks from accessing the alternative NHEJ pathway.

The analysis of the joining mutants K980A and R838A/K839A/R840A makes this model even more compelling. These two mutants, which are the only joining-deficient mutants to appreciably stimulate homologous recombination over wild-type levels in the present study, are also the only ones to produce joints with short sequence homologies and excessive deletions (Huye et al., 2002; Qiu et al., 2001; Yarnall Schultz et al., 2001)-signatures of alternative NHEJ.

These observations provide further evidence that the post-cleavage complex shepherds V(D)J recombination intermediates away from not only homologous recombination but also from alternative NHEJ mechanisms. RAG mutants deficient in this shepherding function dramatically increase the incidence of oncogenic chromosome translocations in developing lymphocytes.

Example Three

RAG-mediated Nicks Efficiently Stimulate Homologous Recombination

Wild-type core and full-length RAG proteins stimulate some homologous recombination on extra-chromosomal and integrated substrates (FIGS. 3 and 4, and see below). Two possible explanations for this phenomenon include that either some signal ends escape from even wild-type post-cleavage complexes, or other V(D)J recombination intermediates, such as nicks, can be initiating recombination. Nicks have long been hypothesized to be capable of initiating homologous exchange (Holliday, 1964; Meselson and Radding, 1975).

Nicks can be the initiating lesions in the CFP assay (See, FIG. 3B). The coding and signal end substrates are identical except for the orientation of the RSS: cleavage of the SE substrate produces blunt signal ends, but cleavage of the CE substrate yields DNA hairpins that must be opened before strand invasion can occur. The fact that the two substrates yielded similar levels of homologous recombination with wild-type core RAG proteins is counter-intuitive if DSBs are the major initiators, since there is an extra step involved in making the covalently sealed coding ends available for recombination that would likely decrease the efficiency of the reaction. Yet it is precisely what is expected if nicks initiate homologous recombination, since the two substrates should be equally susceptible to nicking.

To determine whether nicking could indeed lead to homologous recombination, four RAG-1 nick-only mutants were employed that efficiently perform single-strand nicking but cannot form DSB in vivo (they produce <1% of the levels of DSB formed wild-type RAG proteins, as measured by sensitive ligation-mediated PCR assays) (Huye et al., 2002). All of these "nick-only" mutants (R855A/K856A, R894A, K890A and R972A/K973A) stimulated homologous recombination at least as efficiently as their wild-type counterparts on the extrachromosomal SE substrate (FIG. 6A). Further, three out of four were expressed at wild-type levels according to western blot (FIG. 11). Similar results were obtained with a RAG-2 nick-only mutant, K38A/R39A (Qiu et al., 2001).

The nick-only mutants do not produce DSB detectable by Southern blotting (FIG. 6B and longer exposure beneath) or ligation-mediated PCR (Huye et al., 2002). As expected, no detectable DSB formation is observed with nick-only RAG mutants. This finding is confirmed by overexposing the blot, which revealed no cleavage products generated by the nick-only RAG mutants. These same nick-only mutants proved even better than wild-type full-length and core RAG proteins at stimulating homologous recombination on an SE substrate stably integrated into the genome (FIG. 7, right side).

The next set of experiments took a complementary approach. Instead of using nick-only RAG proteins, a nick-only substrate was used (i.e., a single 12-RSS, which readily undergoes nicking in vitro (Cuomo et al., 1996; Ramsden et al., 1996) but yields very poor DSB formation in vivo (Steen et al., 1997)). The 12-RSS substrate gave the same levels of homologous recombination as the SE substrate in extrachromosomal assays (FIG. 6A) and yielded robust homologous recombination with full-length and core RAG proteins as an integrated substrate (15-fold over the DDE control; FIG. 7, left side). Even when the nick-only mutants are assayed on the single RSS substrate, they are able to stimulate homologous recombination as efficiently as the full-length or core wild-type RAG proteins (FIG. 7). Since neither of two different conditions that block DSB formation by the RAG proteins diminished the efficiency of homologous recombination (singly or in combination), most of the homologous recombination observed with wild-type RAG proteins in this system is elicited not by DSB, but by nicks. This conclusion is further supported from the lack of correlation between levels of DSB and homologous recombination in various situations. Whereas full-length RAG proteins produce ten-fold fewer signal ends than core proteins (FIG. 3C, FIG. 12, and Steen et al., 1999). Both versions of the RAG proteins yield similar levels of homologous recombination (FIGS. 4 and 7). Furthermore, as noted above, I-SceI produces lower levels of DSB than core RAG proteins yet generates significantly higher levels of homologous recombination (FIG. 3B). This highlights the discordance between levels of DSB and homologous recombination initiated by the RAG proteins. These data strengthen the notion that nicks, rather than DSB, are the major RAG-induced initiators of homologous recombination in this system.

The two unstable post-cleavage complex mutants (K980A and R838A/K839A/R840A) stimulate homologous recombination not by releasing DNA ends but by nicking at extremely high levels. First, these two mutants do not nick more than wild-type proteins in vitro (Huye et al., 2002), but they stimulate far more homologous recombination than wild-type proteins or nick-only mutants. Second, neither of these mutants stimulate recombination more than wild-type core RAG proteins on the single-RSS substrate, which allows robust nicking but does not support efficient double-strand break formation. Third, neither of these mutants stimulated recombination above wild-type levels on the CE substrate (FIG. 3B), as expected if they were more proficient at nicking. Thus, the two mutants that destabilize the post-cleavage complex in vitro stimulate homologous recombination in vivo by making the normally sequestered signal ends available.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

Agrawal, A., Eastman, Q. M., and Schatz, D. G. (1998). Transposition mediated by RAG1 and RAG2 and its implications for the evolution of the immune system. Nature 394, 744-751.

Agrawal, A., and Schatz, D. G. (1997). RAG1 and RAG2 form a stable postcleavage synaptic complex with DNA containing signal ends in V(D)J recombination. Cell 89, 43-53.

Arcangioli, B. (1998). A site- and strand-specific DNA break confers asymmetric switching potential in fission yeast. Embo J 17, 4503-4510.

Arcangioli, B., and de Lahondes, R. (2000). Fission yeast switches mating type by a replication-recombination coupled process. Embo J 19, 1389-1396.

Baumann, P., and West, S. C. (1998). DNA End-joining catalyzed by human cell-free extracts. Proc Natl Acad Sci USA 95,14066-14070.

Brandt, V. L., and Roth, D. B. (2002). A recombinase diversified: new functions of the RAG proteins. Curr Opin Immunol 14, 224-229.

Chen, H. T., Bhandoola, A., Difilippantonio, M. J., Zhu, J., Brown, M. J., Tai, X., Rogakou, E. P., Brotz, T. M., Bonner, W. M., Ried, T., and Nussenzweig, A. (2000). Response to RAG-mediated VDJ cleavage by NBS1 and gamma-H2AX. Science 290, 1962-1965.

Cuomo, C. A., Mundy, C. L., and Oettinger, M. A. (1996). DNA sequence and structure requirements for cleavage of V(D)J recombination signal sequences. Molecular and Cellular Biology 16, 5683-5690.

Fabre, F. (1978). Induced intragenic recombination in yeast can occur during the G1 mitotic phase. Nature 272, 795-798.

Ferguson, D. O., and Alt, F. W. (2001). DNA double strand break repair and chromosomal translocation: lessons from animal models. Oncogene 20, 5572-5579.

Ferguson, D. O., Sekiguchi, J. M., Chang, S., Frank, K. M., Gao, Y., DePinho, R. A., and Alt, F. W. (2000). The nonhomologous end-joining pathway of DNA repair is required for genomic stability and the suppression of translocations. Proc Natl Acad Sci U S A 97, 6630-6633.

Frank-Vaillant, M., and Marcand, S. (2002). Transient stability of DNA ends allows nonhomologous end joining to precede homologous recombination. Mol Cell 10, 1189-1199.

Goedecke, W., Eijpe, M., Offenberg, H. H., van Aalderen, M., and Heyting, C. (1999). Mre11 and Ku70 interact in somatic cells, but are differentially expressed in early meiosis. Nat Genet 23, 194-198.

Grawunder, U., and Lieber, M. R. (1997). A complex of RAG-1 and RAG-2 proteins persists on DNA after single-strand cleavage at V(D)J recombination signal sequences. Nucleic Acids Res 25, 1375-1382.

Guidos, C. J., Williams, C. J., Grandal, I., Knowles, G., Huang, M. T. F., and Danska, J. S. (1996). V(D)J recombination activates a p53-dependent DNA damage checkpoint in scid lymphocyte precursors. Genes Dev 10, 2038-2054.

Haber, J. E. (1999). DNA repair. Gatekeepers of recombination. Nature 398, 665, 667.

Han, J.-O., Erskine, L. A., Purugganan, M. M., Stamato, T. D., and Roth, D. B. (1998). V(D)J recombination intermediates and non-standard products in XRCC4-deficient cells. Nucleic Acids Res 26, 3769-3775.

Han, J.-O., Steen, S. B., and Roth, D. B. (1997). Ku86 is not required for protection of signal ends or for formation of nonstandard V(D)J recombination products. Mol Cell Biol 17, 2226-2234.

Hesse, J. E., Lieber, M. R., Gellert, M., and Mizuuchi, K. (1987). Extrachromosomal DNA substrates in pre-B cells undergo inversion or deletion at immunoglobulin V(D)J joining signals. Cell 49, 775-783.

Hiom, K., and Gellert, M. (1998). Assembly of a 12/23 paired signal complex: A critical control point in V(D)J recombination. Molecular Cell 1, 1011-1019.

Hiom, K., Melek, M., and Gellert, M. (1998). DNA transposition by the RAG1 and RAG2 proteins: a possible source of oncogenic translocations. Cell 94, 463-470.

Holliday, R. (1964). A mechanism for gene conversion in fungi. Genet Res Camb 5, 282-304. Hostager, B. S., Haxhinasto, S. A., Rowland, S. L., and Bishop, G. A. (2003). Tumor necrosis factor receptor-associated factor 2 (TRAF2)-deficient B lymphocytes reveal novel roles for TRAF2 in CD40 signaling. J Biol Chem 278, 45382-45390.

Huye, L. E., Purugganan, M. M., Jiang, M. M., and Roth, D. B. (2002). Mutational analysis of all conserved basic amino acids in RAG-1 reveals catalytic, step arrest, and joining-deficient mutants in the V(D)J recombinase. Mol Cell Biol 22, 3460-3473.

Jasin, M. (1996). Genetic manipulation of genomes with rare-cutting endonucleases. Trends Genet 12, 224-228.

Jones, J. M., and Gellert, M. (2001). Intermediates in V(D)J recombination: a stable RAG 1/2 complex sequesters cleaved RSS ends. Proc Natl Acad Sci U S A 98, 12926-12931.

Kabotyanski, E. B., Gomelsky, L., Han, J.-O., Stamato, T. D., and Roth, D. B. (1998). Double-strand break repair in Ku86- and XRCC4-deficient cells. Nucleic Acids Res 26, 5333-5342.

Landree, M. A., Wibbenmeyer, J. A., and Roth, D. B. (1999). Mutational analysis of RAG-1 and RAG-2 identifies three active site amino acids in RAG-1 critical for both cleavage steps of V(D)J recombination. Genes Dev 13, 3059-3069.

Lee, S. S., Fitch, D., Flajnik, M. F., and Hsu, E. (2000). Rearrangement of immunoglobulin genes in shark germ cells. J Exp Med 191, 1637-1648.Lee, G. S., M. B. Neiditch, S. S. Salus, and D. B. Roth, *RAG proteins shepherd double-strand breaks to a specific pathway, suppressing error-prone repair, but RAG nicking initiates homologous recombination.* Cell, 2004. 117, 171-84.

Leu, T. M., Eastman, Q. M., and Schatz, D. G. (1997). Coding joint formation in a cell-free V(D)J recombination system. Immunity 7, 303-314.

Lewis, S. M. (1994). The mechanism of V(D)J joining: Lessons from molecular, immunological and comparative analyses. Advimmunol 56, 27-150.

Lewis, S. M., and Wu, G. E. (2000). The old and the restless. J Exp Med 191, 1631-1636.

Meselson, M. S., and Radding, C. M. (1975). A general model for genetic recombination. Proc Natl Acad Sci U S A 72, 358-361.

Moynahan, M. E., Pierce, A. J., and Jasin, M. (2001). BRCA2 is required for homology-directed repair of chromosomal breaks. Mol Cell 7, 263-272.

Nacht, M., Strasser, A., Chan, Y. R., Harris, A. W., Schlissel, M., Bronson, R. T., and Jacks, T. (1996). Mutations in the p53 and SCID genes cooperate in tumorigenesisGenes&Development 10, 2055-2066.

Pâques, F., and Haber, J. E. (1999). Multiple pathways of recombination induced by double-strand breaks in *Saccharomyces cerevisiae*. Microbiol Mol Biol Rev 63, 349-404.

Perkins, E. J., Nair, A., Cowley, D. O., Van Dyke, T., Chang, Y., and Ramsden, D. A. (2002). Sensing of intermediates in V(D)J recombination by ATM. Genes Dev 16, 159-164.

Perrin, A., Buckle, M., and Dujon, B. (1993). Asymmetrical recognition and activity of the I-SceI endonuclease on its site and on intron-exon junctions. EMBO J 12, 2939-2947.

Pierce, A. J., Hu, P., Han, M., Ellis, N., and Jasin, M. (2001). Ku DNA end-binding protein modulates homologous repair of double-strand breaks in mammalian cells. Genes Dev 15, 3237-3242.

Pierce, A. J., Johnson, R. D., Thompson, L. H., and Jasin, M. (1999). XRCC3 promotes homology-directed repair of DNA damage in mammalian cells. Genes Dev 13, 2633-2638.

Qiu, J. X., Kale, S. B., Yarnell Schultz, H., and Roth, D. B. (2001). Separation-of-function mutants reveal critical roles for RAG2 in both the cleavage and joining steps of V(D)J recombination. Mol Cell 7, 77-87.

Raghavan, S. C., Kirsch, I. R., and Lieber, M. R. (2001). Analysis of the V(D)J recombination efficiency at lymphoid chromosomal translocation breakpoints. J Biol Chem 276, 29126-29133.

Ramsden, D. A., McBlane, J. F., van Gent, D. C., and Gellert, M. (1996). Distinct DNA sequence and structure requirements for the two steps of V(D)J recombination signal cleavage. EMBO J 15, 3197-3206.

Ramsden, D. A., Paull, T. T., and Gellert, M. (1997). Cell-free V(D)J recombination. Nature 388, 488-491.

Richardson, C., and Jasin, M. (2000). Coupled homologous and nonhomologous repair of a double-strand break preserves genomic integrity in mammalian cells. Mol Cell Biol 20, 9068-9075.

Ristic, D., Modesti, M., Kanaar, R., and Wyman, C. (2003). Rad52 and Ku bind to different DNA structures produced early in double-strand break repair. Nucleic Acids Res 31, 5229-5237.

Roth, D. B. (2000). From lymphocytes to sharks: V(D)J recombinase moves to the germlne. Genome Biol 1, 1014.1011-1014.

Roth, D. B. (2002). Amplifying mechanisms of lymphomagenesis. Mol Cell 10, 1-2.

Roth, D. B. (2003). Restraining the V(D)J recombinase. Nat Rev Immunol 3, 656-666.

Roth, D. B., and Wilson, J. H. (1985). Relative rates of homologous and nonhomologous recombination in transfected DNA. Proc Natl Acad Sci U S A 82, 3355-3359.

Roth, D. B., and Wilson, J. H. (1986). Nonhomologous recombination in mammalian cells: role for short sequence homologies in the joining reaction. Mol Cell Biol 6, 4295-4304.

Rouet, P., Smih, F., and Jasin, M. (1994). Introduction of double-strand breaks into the genome of mouse cells by expression of a rare-cutting endonuclease. Molecular and Cellular Biology 14, 8096-8106.

Sadofsky, M. J., Hesse, J. E., and Gellert, M. (1994a). Definition of a core region of RAG-2 that is functional in V(D)J recombination. Nucleic Acids Res 22,1805-1809.

Sadofsky, M. J., Hesse, J. E., McBlane, J. F., and Gellert, M. (1994b). Expression and V(D)J recombination activity of mutated RAG-1 proteins. Nucleic Acids Res 22, 550.

Sakano, H., Huppi, K., Heinrich, G., and Tonegawa, S. (1979). Sequences at the somatic recombination sites of immunoglobulin light-chain genes. Nature 280, 288-294.

Spanopoulou, E., Zaitseva, F., Wang, F.-H., Santagata, S., Baltimore, D., and Panayotou, G. (1996). The homeodomain region of Rag-1 reveals the parallel mechanisms of bacterial and V(D)J recombination. Cell 87, 263-276.

Steen, S. B., Gomelsky, L., and Roth, D. B. (1996). The 12/23 rule is enforced at the cleavage step of V(D)J recombination in vivo. Genes to Cells 1, 543-553.

Steen, S. B., Gomelsky, L., Speidel, S. L., and Roth, D. B. (1997). Initiation of V(D)J recombination in vivo: role of recombination signal sequences in formation of single and paired double-strand breaks. EMBO Journal 16, 2656-2664.

Steen, S. B., Han, J.-O., Mundy, C., Oettinger, M. A., and Roth, D. B. (1999). Roles of the "dispensable" portions of RAG-1 and RAG-2 in V(D)J recombination. Molecular and Cellular Biology 19, 3010-3017.

Strathern, J. N., Weinstock, K. G., Higgins, D. R., and McGill, C. B. (1991). A novel recombinator in yeast based on gene II protein from bacteriophage f1. Genetics 127, 61-73.

Taccioli, G. E., Rathbun, G., Oltz, E., Stamato, T., Jeggo, P. A., and Alt, F. W. (1993). Impairment of V(D)J recombination in double-strand break repair mutants. Science 260, 207-210.

Takata, M., Sasaki, M. S., Sonoda, E., Morrison, C., Hashimoto, M., Utsumi, H., Yamaguchi-Iwai, Y., Shinohara, A., and Takeda, S. (1998). Homologous recombination and non-homologous end-joining pathways of DNA double-strand break repair have overlapping roles in the maintenance of chromosomal integrity in vertebrate cells. EMBO 17, 5497- 5508.

Thompson, C. B. (1995). New insights into V(D)J recombination and its role in the evolution of the immune system. Immunity 3, 531-539.

Tsai, C. L., Drejer, A. H., and Schatz, D. G. (2002). Evidence of a critical architectural function for the RAG proteins in end processing, protection, and joining in V(D)J recombination. Genes Dev 16, 1934-1949.

Tycko, B., and Sklar, J. (1990). Chromosomal translocations in lymphoid neoplasia: a reappraisal of the recombinase model. Cancer Cells 2, 1-8.

Van Dyck, E., Stasiak, A. Z., Stasiak, A., and West, S. C. (1999). Binding of double-strand breaks in DNA by human Rad52 protein. Nature 398, 728-731.

Vanasse, G. J., Concannon, P., and Willerford, D. M. (1999). Regulated genomic instability and neoplasia in the lymphoid lineage. Blood 94, 3997-4010.

Verkaik, N. S., Esveldt-van Lange, R. E., van Heemst, D., Bruggenwirth, H. T., Hoeijmakers, J. H., Zdzienicka, M. Z., and van Gent, D. C. (2002). Different types of V(D)J recombination and end-joining defects in DNA double-strand break repair mutant mammalian cells. Eur J Immunol 32, 701-709.

Villa, A., Sobacchi, C., Notarangelo, L. D., Bozzi, F., Abinun, M., Abrahamsen, T. G., Arkwright, P. D., Baniyash, M., Brooks, E. G., Conley, M. E., etal. (2001). V(D)J recombination defects in lymphocytes due to RAG mutations: severe immunodeficiency with a spectrum of clinical presentations. Blood 97, 81-88.

Wake, C. T., Gudewicz, T., Porter, T., White, A., and Wilson, J. H. (1984). How damaged is the biologically active subpopulation of transfected DNA? Mol Cell Biol 4, 387-398.

Yarnall Schultz, H., Landree, M. A., Qiu, J. X., Kale, S. B., and Roth, D. B. (2001). Joining-deficient RAG1 mutants block V(D)J recombination in vivo and hairpin opening in vitro. Mol Cell 7, 65-75.

Zhu, C., Bogue, M. A., Lim, D.-S., Hasty, P., and Roth, D. B. (1996). Ku86-deficient mice exhibit severe combined immunodeficiency and defective processing of V(D)Jrecombination intermediates. Cell 86, 379-389.

Zhu, C., Mills, K. D., Ferguson, D. O., Lee, C., Manis, J., Fleming, J., Gao, Y., Morton, C. C., and Alt, F. W. (2002). Unrepaired DNA breaks in p53-deficient cells lead to oncogenic gene amplification subsequent to translocations. Cell 109, 811-821.

What is claimed is:

1. A method of stimulating homologous recombination by creating a single-strand nick in a targeted polynucleotide sequence including a recombination signal sequence (RSS) by enzymatic digestion by a mutant V(D)J recombinase chosen from the group consisting of RAG-1 980 and RAG-1 838/839/840, and stimulating homologous recombination.

2. The method according to claim 1, wherein said creating step includes utilizing an expression vector inside of a targeted cell.

3. The method according to claim 1, wherein said creating step includes utilizing purified proteins outside of a targeted cell.

4. A method of increased stimulation of homologous recombination by creating a single-strand nick in a targeted polynucleotide strand including a recombination signal sequence (RSS) with a RAG protein mutation chosen from the group consisting of RAG-1 980 and RAG-1 838/839/840; self-releasing the RAG protein mutation from the targeted polynucleotide strand; and increasing stimulation of homologous recombination.

5. A method of increasing double strand break-initiated gene targeting by inducing a single-strand nick in a targeted polynucleotide sequence including a recombination signal sequence (RSS) by stimulated homologous recombination by a mutant V(D)J recombinase chosen from the group consisting of RAG-1 980 and RAG-1 838/839/840, wherein overall recombination levels are increased.

6. A method of gene targeting by homologously recombining a targeted gene including a recombination signal sequence (RSS) by creating a single-strand nick in the targeted gene by a mutant V(D)J recombinase chosen from the group consisting of RAG-1 980 and RAG-1 838/839/840.

* * * * *

UNITED STATES PATENT AND TRADEMARK OFFICE
CERTIFICATE OF CORRECTION

PATENT NO. : 7,604,995 B2 Page 1 of 1
APPLICATION NO. : 10/887593
DATED : October 20, 2009
INVENTOR(S) : David B. Roth and Gregory S. Lee It is certified that error appears in the above-identified patent and that said Letters Patent is hereby corrected as shown below:

In the Specification:
Column 1, Line 12 should read:
Research in this application was supported in part by a grant from the National Institute of Health (NIH Grant No. R01 AI036420). The Government has certain rights in the invention.

Signed and Sealed this

Seventeenth Day of August, 2010

David J. Kappos
*Director of the United States Patent and Trademark Office*